(12) United States Patent
Hirohara et al.

(10) Patent No.: US 7,677,728 B2
(45) Date of Patent: Mar. 16, 2010

(54) OPHTHALMOLOGIC MEASURING APPARATUS

(75) Inventors: Yoko Hirohara, Tokyo (JP); Toshifumi Mihashi, Tokyo (JP)

(73) Assignee: Kabuhsiki Kaisha Topcon, Tokyo (JP)

( * ) Notice: Subject to any disclaimer, the term of this patent is extended or adjusted under 35 U.S.C. 154(b) by 350 days.

(21) Appl. No.: 11/723,624

(22) Filed: Mar. 21, 2007

(65) Prior Publication Data

US 2007/0229760 A1 Oct. 4, 2007

(30) Foreign Application Priority Data

Mar. 30, 2006 (JP) .............................. 2006-093022

(51) Int. Cl.
*A61B 3/14* (2006.01)
(52) U.S. Cl. ...................... 351/206; 351/209; 351/212; 351/221
(58) Field of Classification Search ................... 351/206
See application file for complete search history.

(56) References Cited

U.S. PATENT DOCUMENTS

| 7,121,666 | B2* | 10/2006 | Tseng et al. | ................. 351/206 |
| 2004/0204674 | A1* | 10/2004 | Anderson et al. | ............. 604/66 |
| 2006/0109423 | A1* | 5/2006 | Wang | ......................... 351/206 |

FOREIGN PATENT DOCUMENTS

| JP | 06-277179 A | 10/1994 |
| JP | 07-136120 A | 5/1995 |
| JP | 08-052112 A | 2/1996 |
| JP | 2005-230328 A | 9/2005 |

OTHER PUBLICATIONS

"The Japanese Society of Ophthalmological Optics (the 41st ), The Japanese Association of Ophthalmic ME (the 20th )" Sep. 3, 2005, V-5.
T. Mihashi et al., "Temporal Changes of Tear Film Break-Up Observed by a Real Time Hartmann-Shack Wavefrong Aberrometer," ARVO, Annual Meeting Fort Lauderdale, Florida, May 4-9, 2003, 2541-B380.
T. Mihashi et al., "Principal Component Analysis of Consecutively Measured Wavefront Aberrations," ARVO, Annual Meeting May 1-5, 2005, 2723-B276.
Richard H. Rand et al., "Mathematical Model of a Placido Disk Keratometer and Its Implication for Recovery of Corneal Topography", Optometry and Vision Science, Nov. 1997, pp. 926-930, vol. 74, No. 11.

* cited by examiner

*Primary Examiner*—Jessica T Stultz
(74) *Attorney, Agent, or Firm*—Foley & Lardner LLP

(57) ABSTRACT

A subject is placed in a more natural state or is encouraged to blink at specified intervals to obtain a measurement result under a fixed condition, and the judgment of the degree of dry eye is facilitated. A measurement part obtains, based on a reflected light flux from a subject eye, optical characteristic data of a two-dimensional vector form representing the time course of each optical characteristic of the subject eye in an blink interval from a certain blink to a next blink with respect to the first to the nth blink intervals. An analysis part one-dimensionally arranges each of the optical characteristic data with respect to the first to the nth blink intervals measured by the measurement part, and arranges the one-dimensional arrangement of the optical characteristic in a p-th blink interval at a p column to create a two-dimensional array, and performs a principal component analysis processing on the two-dimensional array.

11 Claims, 20 Drawing Sheets

FIG. 5

THE LEFT DISPLAYS ONLY
FIRST BLINK INTERVAL FROM
1 SECOND TO 9 SECONDS
ACTUALLY 1 MINUTE
(NOT NECESSARILY 1 MINUTE)

TIME T(S) FROM EXPERIMENT START

| N | M | pupil | 1 | 2 | 3 | 4 | 5 | 6 | 7 | 8 | 9 |
|---|---|---|---|---|---|---|---|---|---|---|---|
| 0 | 0 |  | 6.324 | 6.586 | 6.756 | 6.735 | 6.696 | 6.817 | 6.748 | 6.682 | 6.720 |
| 1 | -1 |  | 0.000 | 0.000 | 0.000 | 0.000 | 0.000 | 0.000 | 0.000 | 0.000 | 0.000 |
| 1 | 1 |  | -4.057 | -4.032 | -3.550 | -3.856 | -3.412 | -3.678 | -3.600 | -3.426 | -3.550 |
| 2 | -2 |  | -29.865 | -30.084 | -29.698 | -29.750 | -29.686 | -29.548 | -29.749 | -29.538 | -29.579 |
| 2 | 0 |  | -0.269 | -0.278 | -0.187 | -0.238 | -0.229 | -0.229 | -0.197 | -0.154 | -0.168 |
| 2 | 2 |  | 0.538 | 0.412 | 0.606 | 0.522 | 0.535 | 0.631 | 0.617 | 0.601 | 0.605 |
| 3 | -3 |  | -0.558 | -0.431 | -0.471 | -0.442 | -0.408 | -0.367 | -0.360 | -0.379 | -0.348 |
| 3 | -1 |  | -0.249 | -0.302 | -0.251 | -0.240 | -0.281 | -0.265 | -0.219 | -0.235 | -0.248 |
| 3 | 1 |  | 0.123 | 0.033 | 0.083 | 0.076 | 0.114 | 0.117 | 0.145 | 0.134 | 0.120 |
| 3 | 3 |  | -0.019 | -0.096 | -0.012 | -0.043 | -0.086 | -0.063 | -0.035 | -0.042 | -0.045 |
| 4 | -4 |  | 0.037 | 0.007 | 0.014 | 0.004 | -0.015 | -0.021 | -0.022 | -0.028 | -0.031 |
| 4 | -2 |  | 0.118 | 0.083 | 0.068 | 0.035 | 0.044 | 0.062 | 0.002 | 0.073 | 0.088 |
| 4 | 0 |  | 0.107 | 0.060 | 0.056 | 0.074 | 0.009 | 0.041 | 0.033 | 0.014 | 0.017 |
| 4 | 2 |  | 0.163 | 0.144 | 0.135 | 0.124 | 0.109 | 0.116 | 0.111 | 0.105 | 0.108 |
| 4 | 4 |  | 0.011 | -0.032 | -0.031 | 0.001 | -0.016 | -0.007 | -0.015 | -0.010 | -0.031 |
| 5 | -5 |  | -0.016 | 0.018 | -0.029 | -0.006 | -0.004 | -0.004 | -0.006 | -0.029 | -0.013 |
| 5 | -3 |  | -0.038 | 0.037 | 0.037 | -0.028 | -0.030 | -0.027 | -0.051 | -0.054 | -0.046 |
| 5 | -1 |  | 0.082 | 0.082 | 0.075 | 0.055 | 0.075 | 0.067 | 0.073 | 0.080 | 0.063 |
| 5 | 1 |  | -0.001 | 0.020 | 0.005 | 0.014 | -0.013 | -0.016 | -0.018 | -0.023 | -0.014 |
| 5 | 3 |  | 0.027 | 0.051 | 0.009 | 0.008 | 0.035 | 0.015 | 0.002 | 0.001 | -0.005 |
| 5 | 5 |  | -0.012 | -0.002 | -0.013 | -0.001 | -0.013 | -0.014 | -0.011 | -0.018 | -0.015 |
| 6 | -6 |  | 0.057 | 0.035 | 0.063 | 0.035 | 0.089 | 0.057 | 0.073 | 0.066 | 0.053 |
| 6 | -4 |  | 0.016 | -0.003 | 0.063 | 0.002 | 0.033 | 0.029 | 0.071 | 0.042 | 0.036 |
| 6 | -2 |  | -0.038 | -0.032 | -0.041 | -0.013 | -0.030 | -0.032 | -0.024 | -0.036 | -0.035 |
| 6 | 0 |  | -0.021 | 0.005 | -0.001 | -0.016 | 0.014 | 0.009 | 0.002 | 0.017 | 0.010 |
| 6 | 2 |  | -0.046 | -0.045 | -0.037 | -0.020 | -0.032 | -0.032 | -0.035 | -0.023 | -0.030 |
| 6 | 4 |  | 0.008 | 0.028 | 0.059 | 0.038 | 0.034 | 0.035 | 0.046 | 0.031 | 0.039 |
| 6 | 6 |  | -0.026 | -0.027 | -0.026 | -0.001 | -0.021 | -0.021 | -0.043 | -0.024 | -0.018 |
|   |   |  | 0.013 | -0.021 | 0.009 | 0.030 | 0.036 | 0.041 | 0.029 | 0.031 | 0.035 |

ORDER AND COEFFICIENT OF ZERNIKE POLYNOMIAL

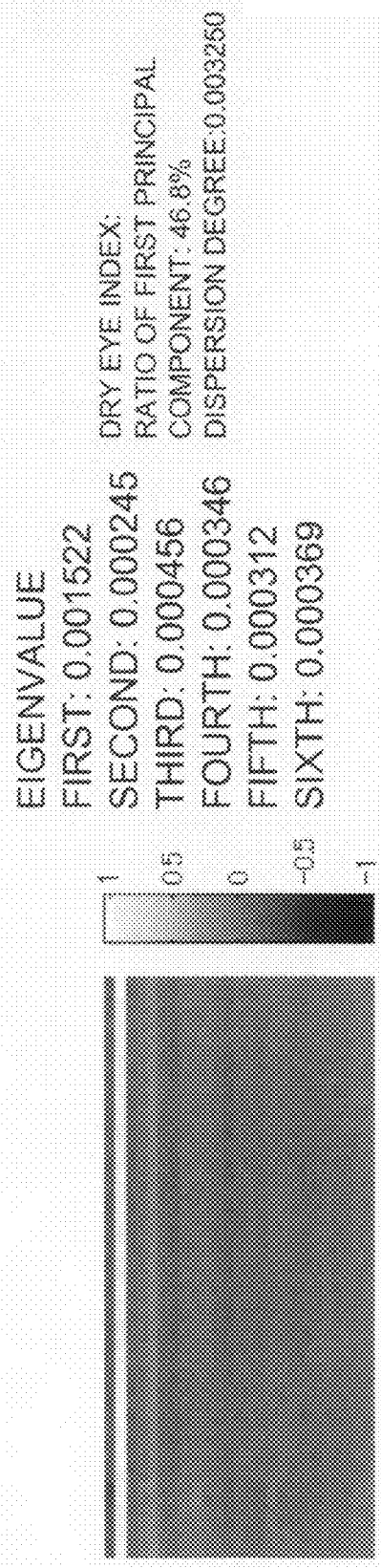
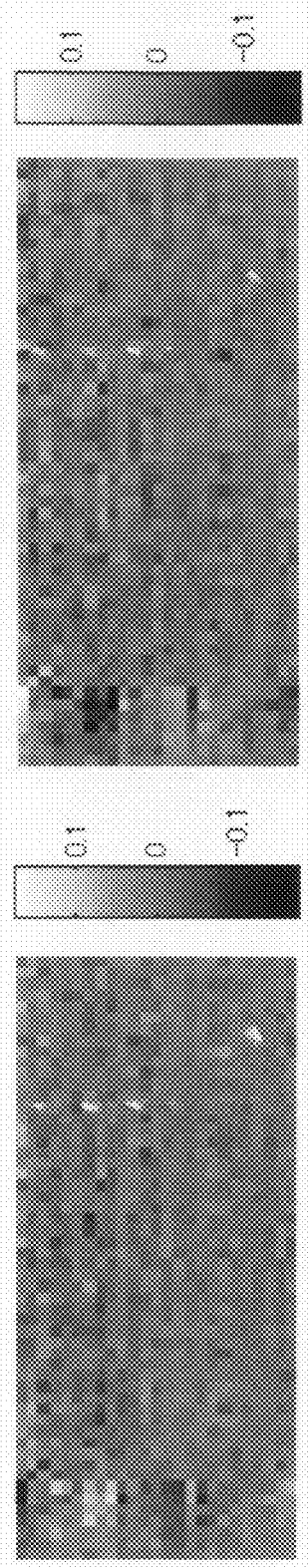
FIG. 9

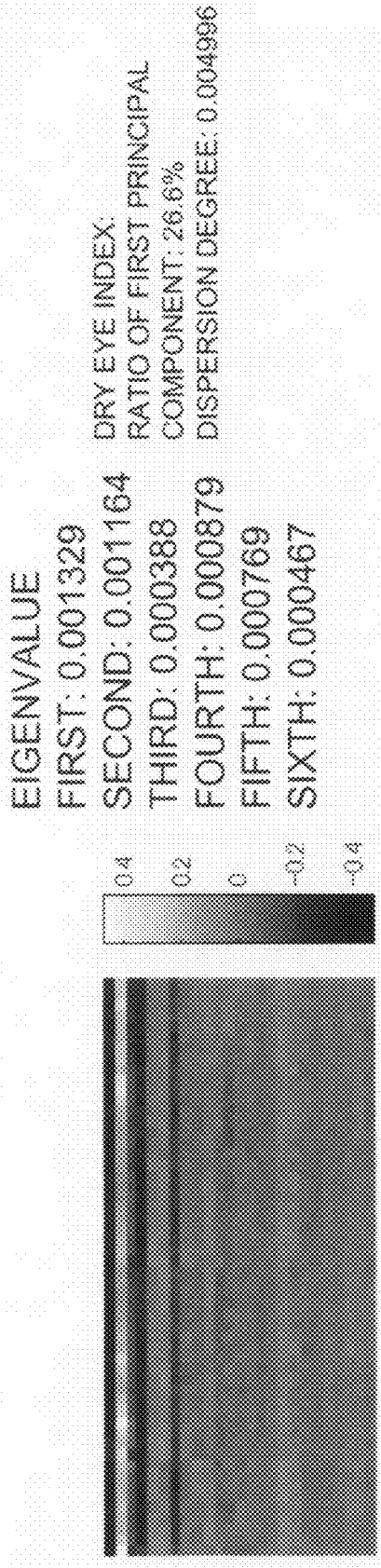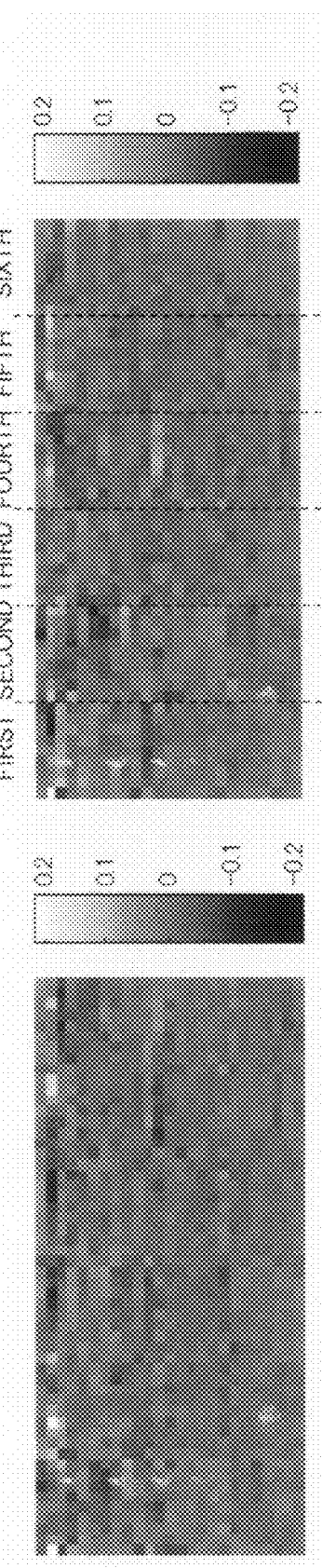
FIG. 10

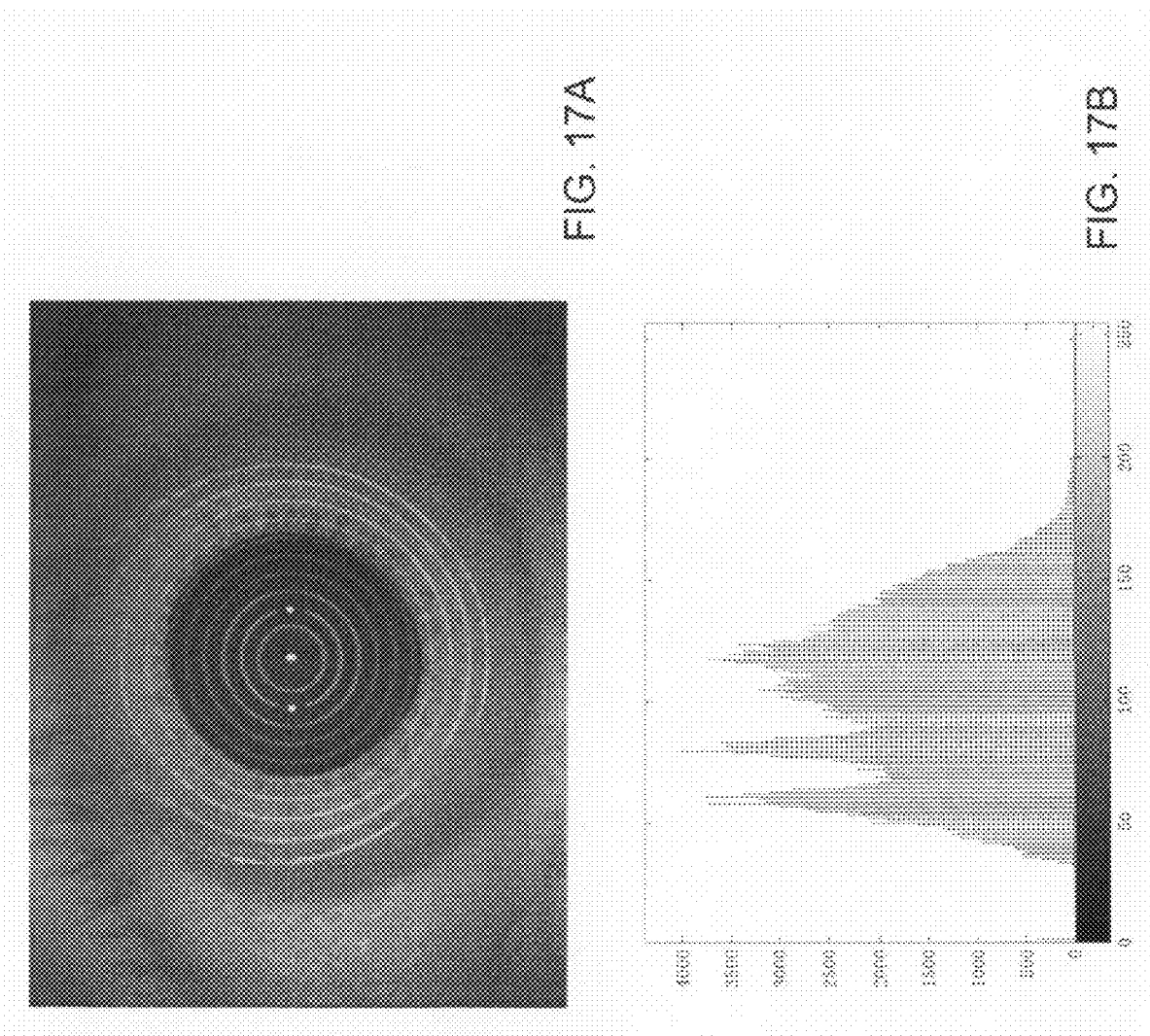

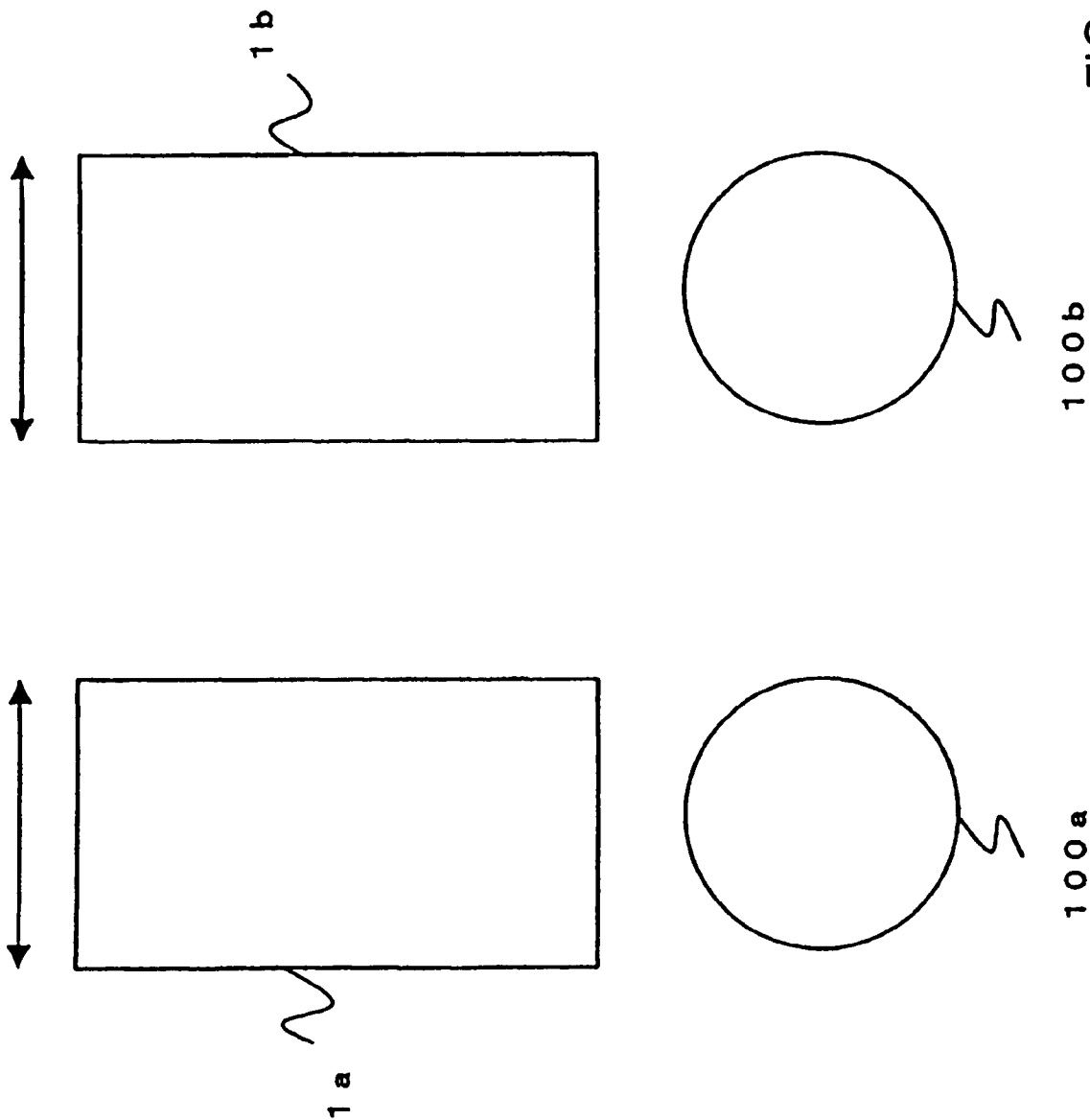

OPHTHALMOLOGIC MEASURING APPARATUS

This application claims priority from Japanese Patent Application No. 2006-093022, filed Mar. 30, 2006, which is incorporated herein by reference in its entirety.

BACKGROUND OF THE INVENTION

1. Field of the Invention

The present invention relates to an ophthalmologic measuring apparatus, and particularly to an ophthalmologic measuring apparatus which performs a principal component analysis of ocular characteristic components changing by blinking, and facilitates judgment on the state of an eye, such as dry eye. In an embodiment of the invention, ocular characteristic components are obtained especially as optical characteristic components such as Zernike polynomials, optical characteristic data obtained plural times in an interval from the start point of timing when a blink starts to a point when a next blink starts are arranged longitudinally, and principal component processing is performed on the longitudinally arranged data.

2. Background Art

Hitherto, as an ophthalmologic measuring apparatus relating to dry eye, following techniques can be mentioned.

Patent document 1 discloses an ophthalmologic measuring apparatus which quantitatively measures fluorescence intensity from a cornea and tear fluid of a subject eye to which a specified fluorescence agent is applied. Patent document 2 discloses an ophthalmologic measuring apparatus which observes a color image of an interference pattern due to interference of reflected light between the front surface and back surface of a lipid layer, so that the state of the lipid layer of the subject eye, the state of flow of tear fluid and the like can be known, and a simple diagnosis of a local dry eye can be easily performed in a non-contact manner. Patent document 3 discloses an ophthalmologic tear observation apparatus in which only a signal light reflected from a tear film of a subject eye is made incident on a CCD, so that shading does not occur in an observation field, and a clear tear interference pattern without disturbance light can be observed in a wide observation field.

Patent document 4 discloses an ophthalmologic apparatus in which a subject is encouraged to blink at specified intervals while he/she is in a more natural state, a measurement result under a fixed condition is obtained, and a change with the passage of time for each individual or comparison of measurement results between different persons can be made more meaningfully.

Further, with respect to the principal component analysis, although non-patent document 1 discloses the application of the principal component analysis to the analysis of a time change in human eye wavefront aberration, the possibility of its usability is merely suggested, and a specific configuration is not clarified.

Patent document 1: JP-A-6-277179
Patent document 2: JP-A-7-136120
Patent document 3: JP-A-8-52112
Patent document 4: JP-A-2005-230328
Non-Patent document 1: "41st The Japanese Society of Ophthalmological Optics, 20th Ophthalmologic ME Society, Joint Society General Meeting, Abstracting Journal", Sep. 3, 2005, page 42

However, in the related art, merely the time change of the ocular aberration is seen, and as the ophthalmologic measuring apparatus used for the clinic of dry eye, it can not be said that demands relating to the judgment of the state of dry eye are sufficiently satisfied.

SUMMARY OF THE INVENTION

In view of the above, the invention has an object to provide an ophthalmologic measuring apparatus in which a measurement result is obtained under a fixed condition while a subject is in a more natural state, or a subject is encouraged to blink at specified periods and a measurement result under a fixed condition is obtained, judgment of the degree of dry eye is more facilitated, and meaningful measurement can be realized. The invention has another object to provide an ophthalmologic measuring apparatus which further includes an analysis part so that diagnosis assistance of dry eye useful for clinic is performed, and automatic diagnosis is also enabled.

According to first solving means of the invention, there is provided an ophthalmologic measuring apparatus which includes an illuminating optical system including an illuminating light source to illuminate a subject eye, a light receiving optical system including a light receiving part to receive a reflected light flux from the subject eye illuminated with an illumination light flux of the illuminating optical system and to form a received light signal, a measurement part that obtains, based on the received light signal formed by the light receiving part, optical characteristic data of a two-dimensional matrix form to represent the time course of each optical characteristic of the subject eye in a blink interval from a blink to a next blink with respect to a first to an n-th (n is an integer of 2 or larger) blink intervals, an analysis part that one-dimensionally arranges each of the optical characteristic data with respect to the first to the n-th blink intervals measured by the measurement part, arranges a one-dimensional vector of the optical characteristic in a p-th ($1 \leq p \leq n$) blink interval at a p-th column to create a two-dimensional array, and performs a principal component analysis processing on the two-dimensional matrix, and a display part to display a processing result of the analysis part.

According to the invention, there can be provided the ophthalmologic measuring apparatus in which the measurement result is obtained under the fixed condition while the subject is in the more natural state, or the subject is encouraged to blink at the specified intervals and the measurement result under the fixed condition is obtained, the judgment of the degree of the dry eye is facilitated, and the meaningful measurement can be realized. According to the invention, since the analysis part is further provided, the diagnosis assistance of the dry eye useful for the clinic is performed, and the automatic diagnosis can also be enabled.

BRIEF DESCRIPTION OF THE DRAWINGS

FIG. 5 is a view showing a time change in coefficients of Zernike polynomials.

FIG. 9 is a view of the result of principal components of a normal example.

FIG. 10 is a view of the result of principal components of slight dry eye.

FIGS. 17A and 17B are explanatory views concerning a histogram when a blink does not occur.

FIG. 20 is a structure view of an ophthalmologic system (2) for both-eye simultaneous measurement.

DETAILED DESCRIPTION OF THE INVENTION

1. Outline (Blink Interval Data)

As wavefront aberration measurement in a blink interval from a certain blink to a next blink, the following two methods can be mentioned.

(1) Data in a Blink Interval by a Blink sign

First Embodiment

In this case, in conformity to a sign signal such as a metronome sound, a subject blinks at, for example, intervals of 10 seconds. At this time, measurement is performed at, for example, intervals of 1 second, and a measurement time is made one minute.

(2) Data in a Natural Blink Interval

Second Embodiment

In this case, a natural blink of a subject is detected, measurement is performed in a period from a certain blink to a next blink, a change in aberration is extracted with respect to a common time from the blink, and a principal component analysis is performed.

(Ocular Wavefront, Corneal Wavefront, and Combination of Both)

As wavefront aberration measurement data which change with the passage of time and on which the principal component analysis is performed, there are conceivable a wavefront aberration (corneal wavefront measurement) generated from the front side of a cornea, which can be measured by a Placido ring type corneal shape measuring apparatus or the like, a wavefront aberration (ocular wavefront measurement) generated from the whole ocular optical system, which can be measured by a Shack-Hartmann wavefront sensor or the like, and both the wavefront aberrations (both-wavefront measurement) of the combination of these two kinds of measurements.

Hereinafter, embodiments of an ophthalmologic measuring apparatus to perform various wavefront measurements as described above will be described.

2. Structure of an Optical System

Figure 1:
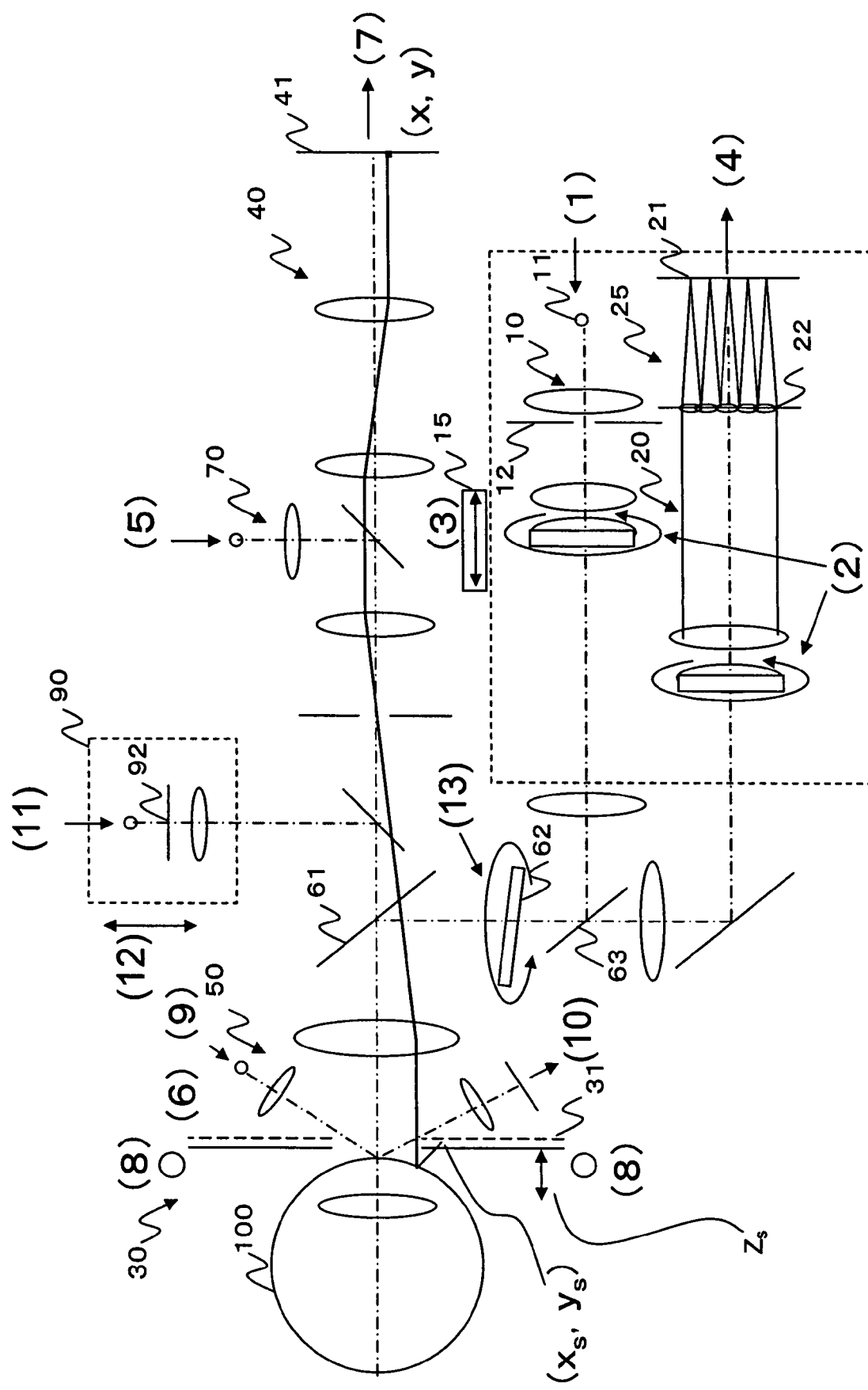
FIG. 1 is a structural view of an optical system of an ophthalmologic measuring apparatus.

FIG. 1 is a structural view of an optical system of an ophthalmologic measurement apparatus.

The ophthalmologic measurement apparatus includes a first illuminating optical system 10, a first light source part 11, a first measurement part 25, an anterior eye part illuminating part 30, an anterior eye part observation part 40, a first adjustment optical part 50, a second adjustment optical part 70, and an index optical part 90. Besides, the first measurement part 25 includes a first light receiving optical system 20 and a first light receiving part 21. Incidentally, with respect to a subject eye 100, a retina (eyeground) and a cornea (anterior eye part) are shown. Besides, the relation among coordinates (x, y), coordinates $(x_s, y_s)$, a distance $Z_s$ and the like will be described later.

Hereinafter, the respective parts will be described in detail.

The first illuminating optical system 10 is for illuminating a minute area on the retina of the subject eye 100 with a light flux from the first light source part 11. The first illuminating optical system 10 includes, for example, a condensing lens, a variable cylinder lens, and a relay lens.

The first light source part 11 emits the light flux with a first wavelength. It is desirable that the first light source part 11 has a high spatial coherence and a not high temporal coherence. Here, as an example, an SLD (Super Luminescence Diode) is adopted for the first light source part 11, and a point light source having high luminescence can be obtained. Incidentally, the first light source part 11 is not limited to the SLD, and a laser light source having a high spatial coherence and a high temporal coherence can also be used by inserting a rotation diffused plate, a declination prism (D prism) or the like to suitably lower the temporal coherence. Further, an LED having a not high spatial coherence and a not high temporal coherence can also be used, if light quantity is sufficient, by inserting a pinhole or the like at a position of a light source in an optical path. Besides, as a wavelength of the first light source part 11 for illumination, for example, a wavelength (for example, 780 nm or 860 nm) of an infrared range can be used.

The first light receiving optical system 20 is for receiving, for example, the light flux reflected and returned from the retina of the subject eye 100 and for guiding it to the first light receiving part 21. The first light receiving optical system 20 includes, for example, a first conversion member 22 (for example, a Hartmann plate), an afocal lens, a variable cylinder lens, and a relay lens. The first conversion member 22 is a wavefront conversion member including a lens part for converting the reflected light flux into at least 17 beams when higher order aberrations of fourth order or higher are obtained. As the first conversion member 22, plural micro Fresnel lenses disposed on a plane orthogonal to an optical axis can be used. The first conversion member 22 may include a short focal point and/or high density lens part in addition to a long focal point or high sensitivity one. The reflected light from the retina is condensed on the first light receiving part 21 through the first conversion member 22. The first light receiving part 21 is for receiving the light passing through the first conversion member 22 from the first light receiving optical system 20 and for generating a first signal. Incidentally, the front side focal point of the afocal lens 42 is substantially coincident with the pupil of the subject eye 100.

A movement part 15 moves a portion, as one body, surrounded by a dotted line of FIG. 1 including the first illuminating optical system 10 and the first light receiving optical system 20. For example, it is assumed that the light flux from the first light source part 11 is reflected at a point where it is condensed, they are moved in the direction in which a signal peak at the first light receiving part 21 becomes high, while the relation that the signal peak at the light receiving part 21 due to the reflected light becomes maximum is kept, and they can be stopped at a position where the intensity becomes maximum. Besides, the first illuminating optical system 10 and the first light receiving optical system 20 may be individually moved, and it is assumed that for example, the light flux from the first light source part 11 is reflected at the point where it is condensed, they are moved in the direction where the signal peak at the first light receiving part 21 becomes high, while the relation that the signal peak at the first light receiving part 21 due to the reflected light becomes maximum is kept, and they can be stopped at the position where the intensity becomes maximum.

With respect to the incident light on the subject eye 100 from the first light source part 11, a diaphragm 12 is made eccentric so that an incident position of the light flux is changed to a direction orthogonal to the optical axis, the vertex reflection of the lens and the cornea is prevented, and the noise can be suppressed. The diaphragm 12 has a diameter smaller than the effective range of the Hartmann plate 22, and is designed so that a so-called single path aberration measurement in which the aberration of an eye has an influence on only a light receiving side can be established.

Incidentally, after the incident light beam emitted from the first light source part 11 comes to have a light path common to a measurement light beam diffused and reflected from the retina, it paraxially travels in the same way as the measurement light beam diffused and reflected from the retina. However, in the single path measurement, the diameters of the respective light beams are different from each other, and the beam diameter of the incident light beam is set to be rather small as compared with the measurement light beam. Specifically, the beam diameter of the incident light beam is, for example, about 1 mm at the pupil position of the subject eye 100, and the beam diameter of the measurement light beam can be about 7 mm. Incidentally, by suitably disposing an optical system, a double path measurement can also be performed.

The anterior eye part illuminating part 30 includes a second light source part 31 for emitting a light flux with a second wavelength and illuminates the anterior eye part with the light flux from the second light source part 31 and with a predetermined pattern by using, for example, a Placido disk, a kerato-ring or the like. In the case of the kerato-ring, a pattern of only the vicinity of the center of curvature of the cornea can be obtained by a corneal-image. Incidentally, the second wavelength of the light flux emitted from the second light source part 31 is different from, for example, the first wavelength (here, 780 nm or 860 nm) and a long wavelength can be selected (for example, 940 nm).

The anterior eye part observation part 40 includes a third light receiving part 41 constituted by, for example, a relay lens, a telecentric diaphragm and a CCD, and observes the light flux which is originated from, for example, the pattern of the Placido disk, the kerato-ring or the like by the anterior eye part illuminating part 30 and is reflected and returned from the anterior eye part of the subject eye 100. Incidentally, by placing the telecentric diaphragm, the diameter of pupil can be measured with accuracy.

The first adjustment optical part 50 is for mainly performing a working distance adjustment, and includes a light source part, a condensing lens, and a light receiving part. Here, the working distance adjustment is performed in such a manner that for example, a parallel light flux emitted from the light source part and close to the optical axis is irradiated to the subject eye 100, and the light reflected from the subject eye 100 is received by the light receiving part through the condensing lens. Besides, in the case where the subject eye 100 is in a suitable working distance, a spot image from the light source part is formed on the optical axis of the light receiving part. On the other hand, in the case where the subject eye 100 goes out of a suitable working distance, a spot image from the light source part is formed above or below the optical axis of the light receiving part. Incidentally, since the light receiving part has only to detect a change of a light flux position on a plane containing the light source part, the optical axis, and the light receiving part, for example, a one-dimensional CCD disposed on this plane, a position sensing device (PSD) or the like can be applied.

A beam splitter 61 is constructed by, for example, a dichroic mirror which reflects the light flux with the first wavelength and is transparent to the light flux with the second wavelength. Besides, there is disposed a rotary prism 62 for uniforming the light subjected to uneven reflection from the retina. A beam splitter 63 is constructed by a mirror (for example, a polarizing beam splitter) which reflects the light flux from the first light source part 11 and is transparent to the light flux reflected and returned from the retina of the subject eye 100.

The second adjustment optical part 70 is for performing, for example, an alignment adjustment in an XY direction, and includes an optical source part for alignment, a lens, and a beam splitter.

The index optical part 90 includes an optical path for projecting, for example, a scenery chart of the subject eye 100, or an index for fixation or fogging, and includes a light source part (for example, a lamp), a fixed index 92, and a relay lens. The fixed index 92 can be irradiated to the retina by the light flux from the light source part, and the subject eye 100 is made to observe its image.

In the foregoing optical system, although the description has been given to the case where the incident light beam has a thin single path, the invention can also be applied to an ophthalmologic measurement apparatus in which the incident light beam has a thick double path. At that time, although an optical system is disposed by means of a structure for the double path, the measurement and calculation processing by an arithmetic part is the same.

(Conjugate Relation)

The retina of the subject eye 100, the fixed index 92 of the index optical part 90, the first light source part 11, and the first light receiving part 21 are conjugate to each other. Besides, the ocular pupil (iris) of the subject eye 100, the rotary prism 62, the conversion member (Hartmann plate) 22 of the first light receiving optical system, and the diaphragm 12 of the first illuminating optical system 10 at the measurement light incident side are conjugate to each other.

3. Electrical System

Figure 2:
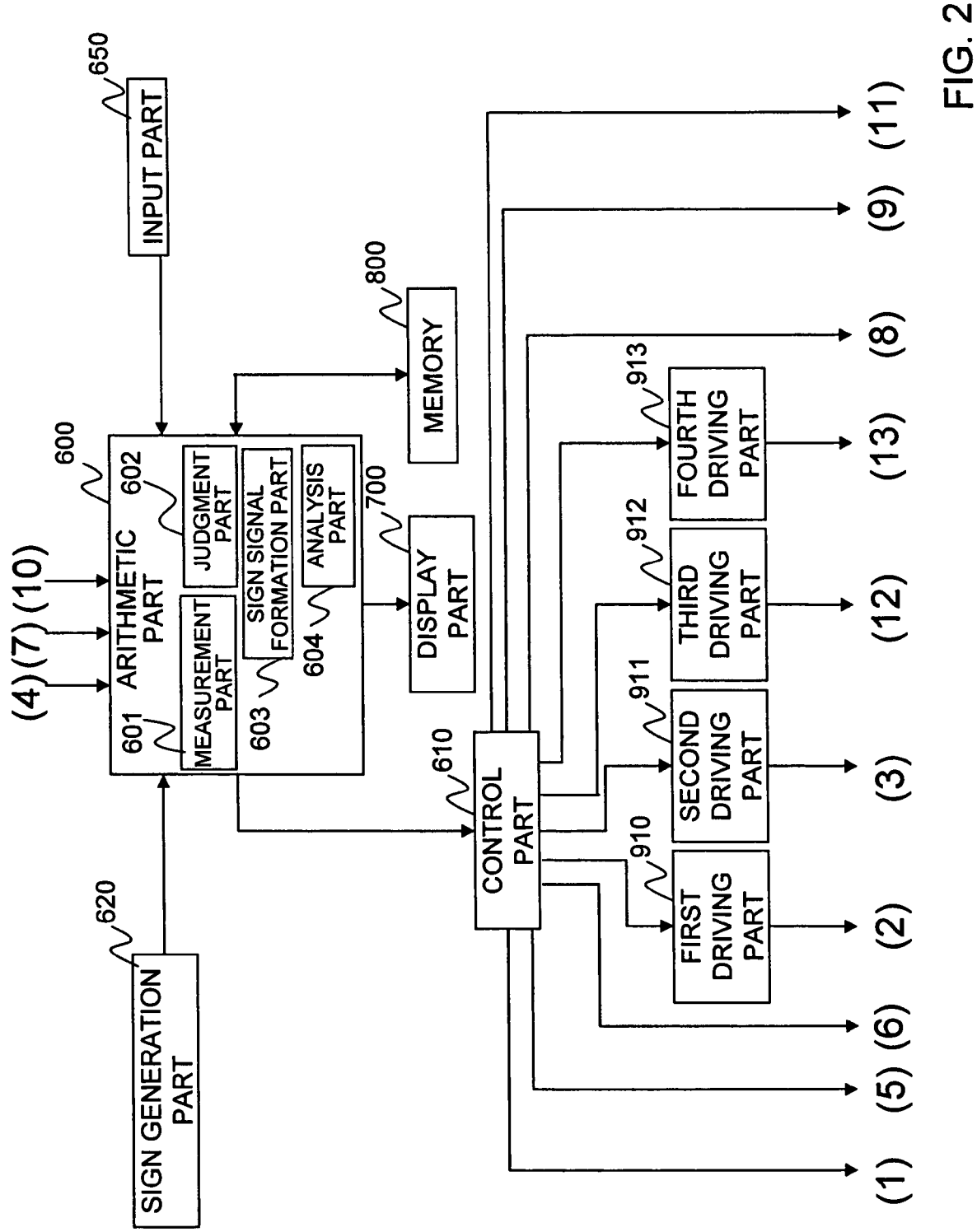
FIG. 2 is a structural view of an electrical system of the ophthalmologic measuring apparatus.

FIG. 2 is a structural view of an electrical system of the ophthalmologic measuring apparatus.

The structure of the electrical system of the ophthalmologic measuring apparatus includes an arithmetic part 600, a control part 610, an input part 650, a display part 700, a memory 800, a first driving part 910, a second driving part 911, a third driving part 912, a fourth driving part 913, and a sign generating part 620. The input part 650 includes a pointing device to indicate a suitable button, an icon, a position, an area or the like displayed on the display part 700, a keyboard to input various data, and the like.

The arithmetic part 600 includes a measurement part 601, a judgment part 602, a sign signal formation part 603 and an analysis part 604.

The measurement part 601 obtains, based on the received light signal formed in the light receiving part such as the first light receiving part 21 and/or the third light receiving part 41, two-dimensional vector form optical characteristic data representing the time course of respective optical characteristics of the subject eye in a blink interval from a certain blink to a next blink with respect to the first to the n-th (n is an integer of 2 or more) blink intervals. The optical characteristic data can be constructed of coefficients of Zernike polynomials.

In one embodiment, the measurement part 601 obtains a corneal shape or a corneal wavefront aberration (including a tear film surface shape and a tear film wavefront aberration) of the subject eye from the received light signal of the first light receiving part plural times at the measurement start point and in a specified period thereafter or to a next blink (corneal wavefront measurement). The judgment part 602 judges the state of dry eye by comparing the time change of the corneal shape from the measurement result of the measurement part 601.

In another embodiment, the measurement part 601 can be constructed to measure the wavefront aberration of the subject eye based on divided light fluxes by the first conversion member 22 from the received light signal of the first light receiving part 21 in a specified period from the start point after a blink of the subject eye or until a next blink (ocular wavefront measurement). In this case, the judgment part 602 is constructed to mainly judge the presence/absence of the blink of the subject eye.

In still another embodiment, the measurement part (wavefront measurement part) 601 performs the measurement of both the wavefront aberrations of the plural corneal wavefront measurements of the subject eye and the ocular wavefront measurement in a specified period or until a next blink.

The judgment part 602 mainly judges the presence/absence of the blink of the subject eye. When detecting the first blink, the judgment part 602 sends its signal to the sign signal formation part 603. The sign signal formation part 603 gives an instruction to generate a sign at specified time intervals to the sign generation part 620 based on the signal. In accordance with the instruction from the sign signal formation part 603, the sign generation part 620 generates the sign to encourage the subject to blink at intervals of a specified period (for example, 10 seconds). The sign may be anything as long as the subject can recognize, and for example, there are conceivable visual light generation, buzzer sounding appealing to the ear, and the like. As an example, in an aural type, in order to provide good timing, for example, rhythmic timing is produced like a metronome, timing is informed by a sound "pip-ipipii" like a telephone or a time signal of a television, or a signal to provide timing at intervals of 1 second is issued, and a tone of a blink sign is issued at intervals of 10 seconds.

The analysis part 604 one-dimensionally arranges the respective optical characteristic data concerning the first to the n-th blink intervals measured by the measurement part 601, arranges a one-dimensional vector of the optical characteristic in the p-th ($1 \leq p \leq n$) blink interval at the p-th column to create a two-dimensional matrix, and performs the principal component analysis processing on the two-dimensional matrix. The analysis part 604 subtracts a time average of each element from each element of the optical characteristic data measured by the measurement part 601 and may form the optical characteristic data. Besides, with respect to the principal components obtained by the principal component analysis processing, for each principal component, reversely to the manner in which each of the optical characteristic data concerning the first to the n-th blink intervals measured by the measurement part 601 is arranged one-dimensionally, the analysis part 604 converts the one-dimensional vector (corresponding to the ninth principal component) at the p-th column into a two-dimensional matrix to represent the time course of each optical characteristic, and arranges the first to the n-th optical characteristic data, whereby the two-dimensional space to represent the time change in the respective optical characteristics can be obtained.

The display part 700 displays the processing result of the analysis part 604. The display part 700 can display a code map based on the two-dimensional space obtained by the analysis part 604. The display part 700 displays, as the code map, typical gray scale codes or color codes of normal, weak dry eye, intermediate dry eye, and serious dry eye, for the judgment of a measured case, on the screen. Alternatively, these gray scale codes or color codes may be displayed on the screen by a simple operation.

The subject may be encouraged to blink by the sign signal formation part 603. By this, the measurement part 601 can measure the optical characteristic of the subject eye changing with the elapsed time from the end of the blink of the subject.

The arithmetic part 600 receives a first signal (4) from the first light receiving part 21, a signal (7) from the anterior eye part observation part 40, and a signal (10) from the first adjustment optical part 50. The arithmetic part 600 receives the first signal (4) from the first light receiving part 21 and the signal (7) from the anterior eye part observation part 40, and obtains the optical characteristic of the subject eye 100 on the basis of, for example, inclination angles of the light fluxes. The arithmetic part 600 suitably outputs signals corresponding to the arithmetical operation results of these or other signals and data to the control part 610 for performing the control of the electrical drive system, and to the display part 700 and the memory 800.

The control part 610 is for controlling the lighting and extinction of the first light source part 11 and the second light source part 31, and for controlling the first driving part 910 to the fourth driving part 913 on the basis of the control signals from the arithmetic part 600. For example, on the basis of the signals corresponding to the arithmetical operation results in the arithmetic part 600, the control part 610 outputs a signal (1) to the first light source part 11, outputs a signal (5) to the second adjustment optical part 70, outputs a signal (6) to the anterior eye part illuminating part 30, outputs signals (8) and (9) to the first adjustment optical part 50, outputs a signal (11) to the index optical part 90, and further outputs signals to the first driving part 910 to the fourth driving part 913.

The first driving part 910 outputs a signal (2) on the basis of the signal (4) inputted to the arithmetic part 600 from the first light receiving part 21, and drives suitable lens movement means to rotate the variable cylinder lens of the first illuminating optical system 10 and the variable cylinder lens of the first light receiving optical system 20. The variable cylinder lens may not be provided.

The second driving part 911 is for moving the first illuminating optical system 10 and the first light receiving optical system 20 in the optical axis direction on the basis of the received light signal (4) inputted to the arithmetic part 600 from the first light receiving part 21, and outputs a signal (3) to the movement part 15, and drives the lens movement means of the movement part 15. The first light receiving optical system 20 is moved in the optical axis direction, so that the compensation of low order aberrations can be performed.

The third driving part 912 is for moving, for example, the index optical part 90, and outputs a signal (12) to a not-shown suitable movement means and drives this movement means. The fourth driving part 913 is for rotating the rotary prism 62, and outputs a signal (13) to a not-shown suitable leans movement means and drives this lens movement means.

4. Measurement Flowchart 4-1. Measurement Flowchart

First Embodiment

Figure 3:
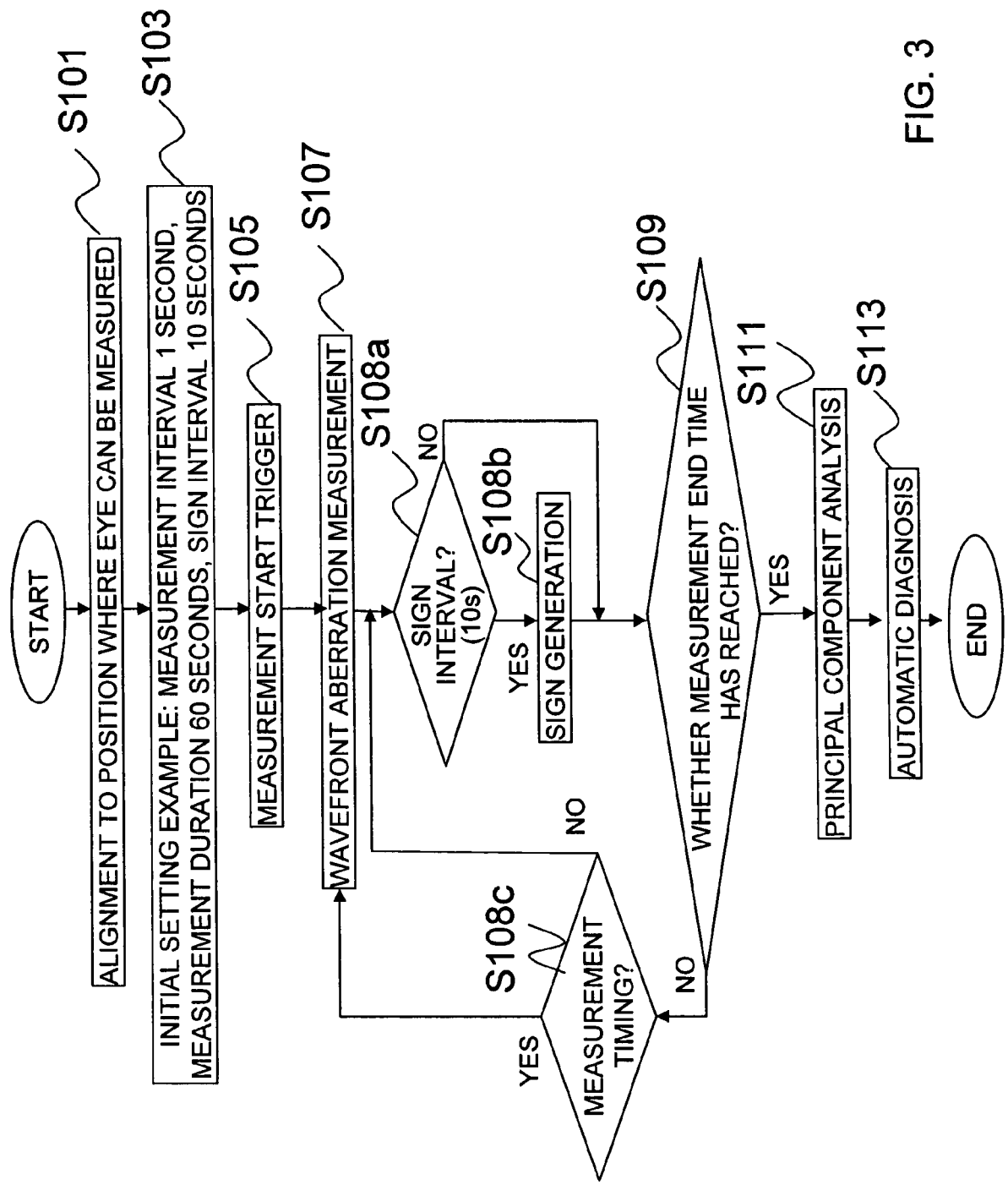
FIG. 3 is a measurement flowchart of a first embodiment.

FIG. 3 shows a measurement flowchart of a first embodiment.

In the first embodiment, blink interval data by a blink sign is measured.

The ophthalmologic measuring apparatus may be constructed to select one of a corneal wavefront measurement mode, an ocular wavefront measurement mode and a both-wavefront measurement mode of a cornea and an eyeball, or may be constructed to be capable of performing measurement in one of or plurality of these modes.

When the subject moves to a measurement position and the measurement is started, the ophthalmologic measuring apparatus is aligned at a position where the eye can be measured (S101). The alignment may be manually or automatically performed. For the wavefront aberration measurement, it is necessary to fix the positions of the cornea and/or the subject eye (retina, ocular fundus, etc.) and the ophthalmologic measuring apparatus within a specified range. The ophthalmologic measuring apparatus is manually or automatically controlled so as to fix the back-and-forth, right-and-left, and up-and-down positions. For example, based on one of or plurality of a Pracido ring (Kerato ring), a light point from infinity, a point of parallel projection, and a contour of the cornea, an operator manually keeps the alignment, or the alignment can be automatically kept by an auto-alignment function of the apparatus itself. In the alignment of step S101, in the corneal wavefront measurement mode, the alignment between the cornea or the anterior eye part and the ophthalmologic measuring apparatus is performed, and in the ocular wavefront measurement mode, although the alignment between the cornea or the anterior eye part and the ophthalmologic measuring apparatus is performed, the alignment between the subject eye (retina, ocular fundus, etc.) and the ophthalmologic measuring apparatus may be performed. Besides, in the both-wavefront measurement mode, although the alignment between the cornea or the anterior eye part and the ophthalmologic measuring apparatus is performed, the alignment of the subject eye (retina, ocular fundus, etc.) and the ophthalmologic measuring apparatus may be performed.

Next, the arithmetic part 600 performs initial setting of the apparatus by the measurement part 601 (S103). The measurement part 601 sets, for example, the measurement interval to 1 second, the measurement time to 60 seconds, and the blink sign signal interval to 10 seconds. When the judgment part 602 detects a blink, a trigger is issued for the measurement start (S105). As the trigger, for example, the measurement start may be performed by the operation of a measurement start button by the operator or the measurer, or the measurement start may be automatically performed by the apparatus itself such as the arithmetic part 600. Besides, the timing of the measurement start is selected and may be previously set from the input part 650. In accordance with the trigger, the measurement part 601 executes the wavefront aberration measurement processing and stores a measurement result into the memory 800 by the arithmetic part 600 (S107).

Here, in the wavefront aberration measurement at step S107, one of the following measurement modes is executed by, for example, previous setting, or the function provided in the measuring apparatus.

(1) Corneal Wavefront Measurement Mode

In this measurement mode, the measurement part 601 measures the corneal shape and the corneal wavefront aberration by the anterior eye observation part 40 and the like. The details of the measurement processing of the wavefront aberration of the corneal shape, more particularly, the tear film surface shape of the corneal surface will be described later.

(2) Ocular Wavefront Measurement Mode

In this measurement mode, the measurement part 601 measures the wavefront aberration of the subject eye by the first light source part 11, the first illuminating optical system 10, the first light receiving optical system 20 and the like.

(3) Both-Wavefront Measurement Mode of the Corneal Wavefront Measurement and the Ocular Aberration Measurement In this measurement mode, the measurement part 601 measures the wavefront aberrations of both the measurement of the corneal shape and the corneal wavefront aberration by the anterior eye observation part 40 and the like and the measurement of the wavefront aberration of the subject eye by the first light source part 11, the first illuminating optical system 10, the first light receiving optical system 20 and the like.

Next, it is judged whether or not the sign interval occurs (S108*a*). Here, in the case of the sign interval, the sign generation part 620 generates a sign (buzzer, flashing of a fixation target, etc.) by the instruction of the sign signal formation part 603 (S108*b*). In the case of the timing when the sign signal is not yet generated, it is judged whether or not the measurement end time has occurred (S109), and in the case where the end time has not occurred, it is judged at step S108*c* whether or not the measurement timing occurs, and when the measurement timing occurs, a return is made to step S107 and the wavefront aberration measurement is performed. In the case where the measurement timing does not occur, the measurement of the wavefront aberration is not performed, and an advance is made to step S108*a*. Here, the arithmetic part 600 repeats the wavefront aberration measurement processing by the measurement part 601 until the measurement end time occurs, and obtains the wavefront aberration of the subject eye (S109). When the measurement end time occurs, the arithmetic part 600 ends the measurement, and a shift is made to step S111 of the principal component analysis.

At step S111, the analysis part 604 reads the measurement result from the memory 800, or obtains the measurement result from the measurement part 601, performs the principal component analysis based on the measurement result, displays the analysis result of the code map and the like on the display part 700, and/or stores it into the memory 800. The details of the principal component analysis will be described later. Next, the analysis part 604 reads the result of the principal component analysis from the memory 800, and performs the automatic diagnosis of dry eye based on that (S113). As the automatic diagnosis, for example, as described later, a dry eye index (for example, a contribution ratio of a first principal component, or the sum of dispersion degrees of all principal components) is determined, and is displayed on the display part 700 or is stored into the memory 800, or the degree of the dry eye is estimated from the typical color codes or gray scale codes of the dry eye displayed on the display part 700. The details of the code map and the dry eye index will be described later.

4-2. Measurement Flowchart

Second Embodiment

Figure 4:
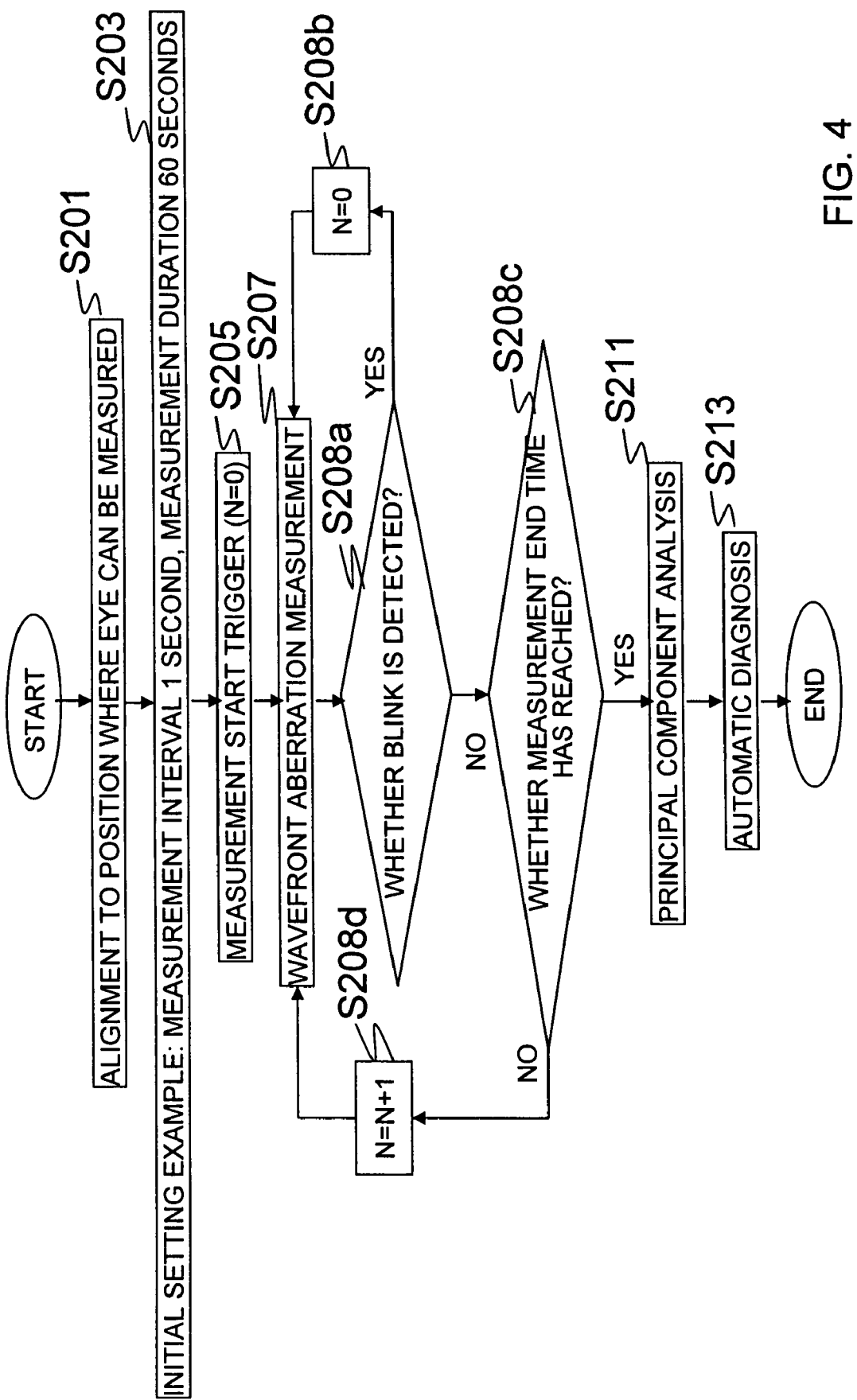
FIG. 4 is a measurement flowchart of a second embodiment.

FIG. 4 shows a measurement flowchart of a second embodiment.

In the second embodiment, natural blink interval data are measured (blink automatic detection). That is, measurement is performed in a period in which the subject naturally blinks, and a change in aberration is extracted with respect to a common time from the blink.

The ophthalmologic measuring apparatus may be constructed to be capable of selecting one of the corneal wavefront measurement mode, the ocular wavefront measurement mode, and the both-wavefront measurement mode of the cornea and eye ball, or may be constructed to be capable of performing measurement in one of or plurality of these modes.

When the subject moves to a measurement position and the measurement starts, the ophthalmologic measuring apparatus is aligned to the position where the eye can be measured (S201). This alignment may be manually or automatically performed. For the wavefront aberration measurement, it is necessary to fix positions of the cornea and/or the subject eye (retina, ocular fundus, etc.) and the ophthalmologic measuring apparatus within a specified range. The ophthalmologic measuring apparatus is manually or automatically controlled so as to fix the back-and-forth, right-and-left, and up-and-down positions. For example, based on one of or plurality of a Pracido ring (Kerato ring), a light point from infinity, a point of parallel projection, a contour of the cornea and the like, the operator manually keeps the alignment, or the alignment can be automatically kept by the auto-alignment function of the apparatus itself. In the alignment at step S201, in the corneal wavefront measurement mode, the alignment between the cornea or the anterior eye part and the ophthalmologic measuring apparatus is performed, and in the ocular wavefront measurement mode, although the alignment between the cornea or the anterior eye part and the ophthalmologic measuring apparatus is performed, the alignment between the subject eye (retina, ocular fundus, etc.) and the ophthalmologic measuring apparatus may be performed. Besides, in the both-wavefront measurement mode, although the alignment between the cornea or the anterior eye part and the ophthalmologic measuring apparatus is performed, the alignment between the subject eye (retina, ocular fundus, etc.) and the ophthalmologic measuring apparatus may be performed.

Next, the arithmetic part 600 performs the initial setting of the apparatus by the measurement part 601 (S203). The measurement part 601 sets, for example, the measurement interval to 1 second and the measurement time to 60 seconds. Alternatively, it is effective for a subject having a short blink interval to make the measurement interval shorter, for example, 0.1 second. When the judgment part 602 detects a blink, a trigger is issued for the measurement start, and a variable for blink detection is set to an initial value (for example, N=0) (S205). As the trigger, for example, the measurement start may be performed by the operation of the measurement start button by the operator or measurer, or the measurement start may be automatically performed by the apparatus itself such as the arithmetic part 600. Besides, the timing of measurement start is selected and may be previously set from the input part 650. In accordance with the trigger, the measurement part 601 executes the wavefront aberration measurement processing, and stores the measurement result into the memory 800 by the arithmetic part 600 (S207). With respect to the wavefront aberration measurement, similarly to the first embodiment, one of the following measurement modes is executed by, for example, previous setting or the function provided in the measuring apparatus:

(1) corneal wavefront measurement mode,
(2) ocular wavefront measurement mode, and
(3) both-wavefront measurement mode of the corneal wavefront measurement mode and the ocular wavefront measurement mode.

Next, in a period in which the measurement part 601 measures the aberration, the judgment part 602 performs blink detection in real time while acquiring the anterior eye image by the anterior eye observation part 40 (S208a). At this time, for example, 100 FPS (the number of captured images per second) can be set. In the case where a blink is detected by the judgment part 602, in order to perform measurement from the point when the blink is detected (for example, for the case where the blink occurs in the measurement interval of 1 second), the arithmetic part 600 returns N to the initial value (for example, N=0) (S208b). On the other hand, in the case where the blink is not detected by the judgment part 602, the arithmetic part 600 judges whether or not a previously set measurement end time has occurred (S208c). In the case where the measurement end time has not occurred, the arithmetic part 600 increments the variable N (in this example, N=N+1) (S208d), a return is made to step S207, and the wavefront aberration measurement of the subject eye is performed. Here, the arithmetic part 600 repeats the wavefront aberration measurement processing by the measurement part 601 until the measurement end time has occurred, and obtains the wavefront aberration of the subject eye (S208c). The arithmetic part 600 ends the measurement when the measurement end time has occurred, and a shift is made to step S211 of the principal component analysis.

At step S211, the analysis part 604 reads the measurement result from the memory 800, or obtains the measurement result from the measurement part 601, performs the principal component analysis based on the measurement result, displays the analysis result of the code map or the like on the display part 700, and/or stores it into the memory 800. The details of the principal component analysis will be described later. Next, the analysis part 604 reads the result of the principal component analysis from the memory 800, and performs automatic diagnosis of dry eye based thereon (S213). As the automatic diagnosis, for example, as described later, a dry eye index (for example, a contribution ratio of the first principal component, or the sum of dispersion degrees of all principal components) is determined, and is displayed on the display part 700 or is stored in the memory 800, or the degree of dry eye is estimated from the typical color codes or gray scale codes of the dry eye displayed on the display part 700. The details of the code map and the dry eye index will be described later.

Although the principal component analysis of step S211 is similar to that of the first embodiment, in the second embodiment, a method of forming a two-dimensional matrix is executed as follows. That is, in the principal component analysis of step S211, the analysis part 604 arranges values of coefficients with the same value of the measurement point N into the same column. For example, when a two-dimensional array is formed, the analysis part 604 extracts data for each blink interval. Then, a matrix of 25 rows by X columns is obtained for the blink interval. The number of X columns is, for example, (blink interval)/(measurement interval).

Here, as a method of forming the two-dimensional matrix of X columns, for example, there are following two methods.

1. Method in which a minimum value of a blink interval to be adopted is previously determined.
2. Method in which after a measurement value is seen, a blink interval to be adopted is determined.

First, a description will be given to "1. Method in which a minimum value of a blink interval to be adopted is previously determined". For example, it is assumed that the blink interval to be adopted is 7 seconds or more. In this case, the analysis part 604 selects only a case where the blink interval is 7 seconds or more, and uses data up to 7 seconds therein. For example, when the measurement interval is 1 second, the unit of the principal component analysis becomes 25 rows by 7 columns. This is transformed into a one-dimensional vector similarly to the case of the fixed blink interval of the first embodiment. Then, the vector having 175 elements is formed. When the analysis part 604 arranges such vectors the number of which is the number of the previously selected blink intervals, a two-dimensional matrix for the principal component analysis is formed.

Next, a description will be given to "2. Method in which after a measurement value is seen, a blink interval to be adopted is determined". In this case, with respect to plural blink intervals, the analysis part 604 sets an interval obtained as a rough blink interval. Alternatively, when the minimum value of the blink interval is a specified value (for example, 5 seconds) or more, the minimum value of the blink interval is made the measurement interval, and when it is not higher than the specified value, only values not lower than the specified value are made analyzable, and the minimum value therein is made the measurement interval. In addition, with respect to the plural blink intervals, it is judged whether data satisfies a condition of measurement interval and the like, and setting is performed. A specified number of data of blink intervals are adopted and the two-dimensional matrix is created.

5. Principal Component Analysis 5-1. Outline

The principle component analysis (PCA) is a method in which correlation among many variables is analyzed, and variations in these variables are constructed of the smallest possible variables. By the principal component analysis, the compression of information, and reduction of dimensions can be performed.

As in the related art, although the change in the aberrations of dry eye can be evaluated by the total aberration amount, in the case where all aberrations are used, there is a case where a quantitative feature of the aberrations, for example, information on a portion of the pupil where the wavefront advances is lost. Since it is considered that the local information of the pupil relating to the way of advancing of the wavefront is one of important features in the evaluation of dry eye, it is desired to develop a processing in which such information is not lost.

In general, it is very effective to expand the aberration in the Zernike polynomials. Especially, when the aberration is statically considered, the Zernike polynomial is a very useful analysis tool since it is an orthogonal polynomial in the pupil of an optical system, and well matches with Zeidel aberrations in low-order terms.

However, in the analysis of the time change of the aberration, a situation somewhat varies. Since the information amount of the whole measurement is the product of the number of terms of the Zernike polynomials and the number of times of measurement in the time direction, it becomes a vast amount, and it is conceivable that a person can not easily make a judgment by seeing the analysis result. Besides, there is a correlation between time changes of coefficients of respective terms of the Zernike polynomial. That there is a correlation means that the influence of a change appears in the change of plural terms, and it would not be necessarily easy for a person to accurately judge the correlation.

In this embodiment, it is proposed that with respect to aberration measurement values taken successively, information is compressed by the principal component analysis.

5-2. Analysis Example

As described before, in the case where the blink interval data by the blink sign is acquired, the measurement is similar to the foregoing, and the subject blinks at intervals of, for example, 10 seconds, the measurement time is 1 minute, and the number of times of measurement of wavefront aberration is once per second. At the measurement, a fixation target is presented to the subject, and adjustment and intervention of an ocular movement are prevented to the utmost. In this example, the analysis uses 25 terms of the secondary-order to sixth-order Zernike polynomials, and 54 points in the time direction for the principal component analysis (image with a blink is removed).

FIG. 5 is a view showing the time change of coefficients of the Zernike polynomials.

N, M of the first row denotes the order of the Zernike polynomial, and a numeral denotes a time from the measurement start. Here, results from 1 second to 9 seconds are displayed. Actually, there are measurement data up to 59 seconds.

This drawing shows results of the wavefront analysis using the Zernike polynomials, while the measurement of a normal person is used as an example. For the principal component analysis, among the coefficients of the Zernike polynomials, as an example, 25 terms of from the second order to sixth order are used. Incidentally, coefficients to be used can be suitably selected according to necessity such as a symptoms or the state of the subject eye.

5-3. Processing of the Principal Component Analysis

In the well-known principal component analysis to the elapsed time wavefront aberration, there is a case where time dependency of aberration change is not necessarily effectively used. Besides, in the conventional method, there are many outputs to be reviewed, and there is a case where it is inconvenient for a clinical use. In this embodiment, in order to improve these, there is proposed a method in which the arrangement of the coefficients of the Zernike polynomials and the time are processed as a two-dimensional data set as they are.

Figure 6:
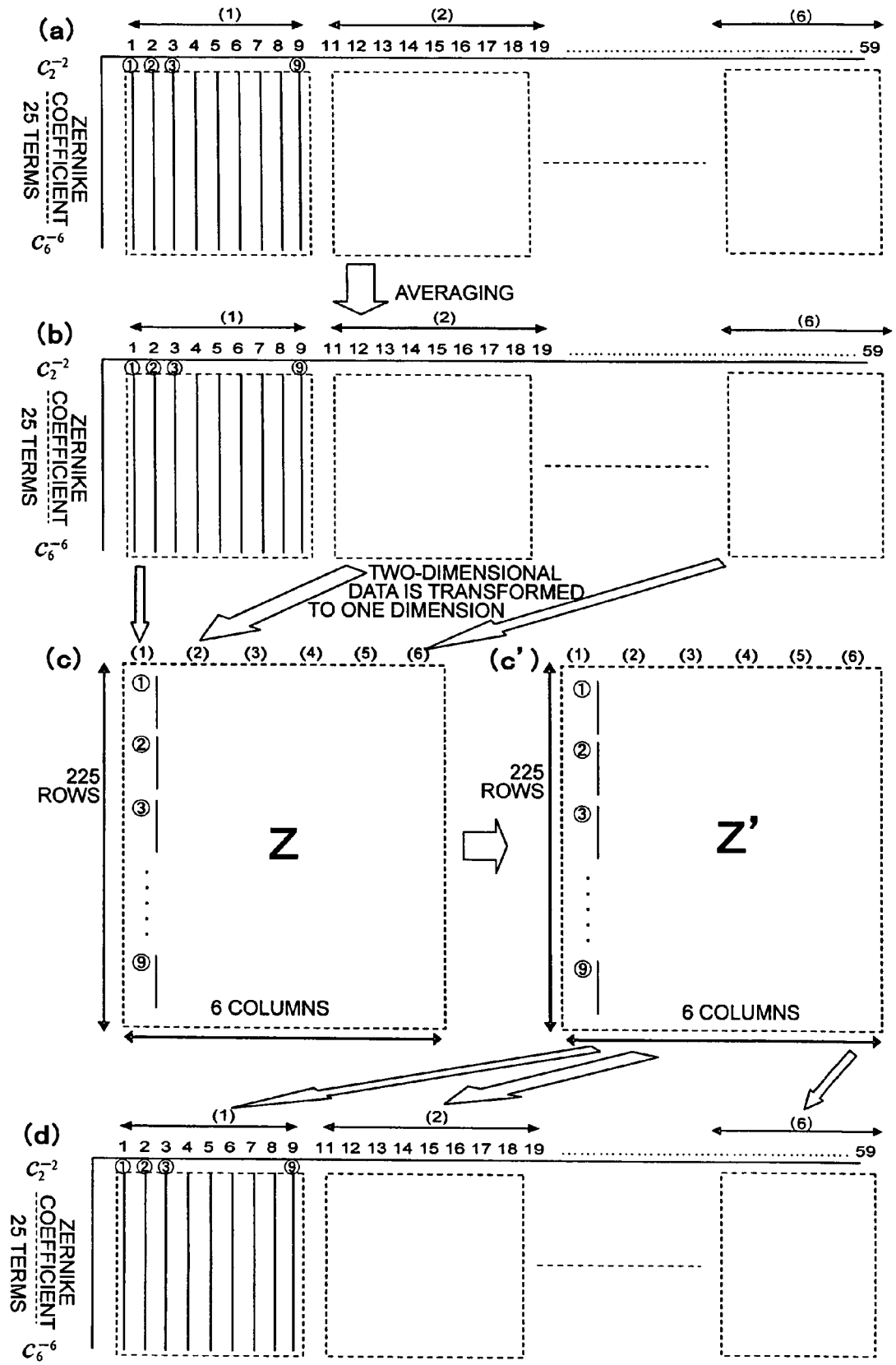
FIG. 6 is explanatory view concerning a creation method of an analysis value in a principal component analysis.

FIG. 6 is explanatory view concerning a creation method of analysis values in the principal component analysis.

In the following embodiment, as an example, consideration is given to a method in which in a table of time change of coefficients of the Zernike polynomials, a matrix of 25 rows by 9 columns (25 coefficients, 9 measurement points in the time direction) corresponding to one blink interval is made one measurement unit ((a) in FIG. 6). Here, an average value of the coefficients in the time direction is subtracted from the respective coefficients of the matrix ((b) in FIG. 6). Incidentally, in addition to the subtraction of the average value, a processing for indicating a different from a suitable average value can also be applied, or the processing as stated above may be omitted. The matrix of 25 rows by 9 columns is transformed into a one-dimension array like the first column of (c) in FIG. 6, that is, a vector. Further, some vectors made of different blink intervals are arranged as in (c) in FIG. 6, so that a two-dimensional matrix Z is formed. Here, the principle component analysis is applied to these sets (two-dimensional matrix).

(Principle Component Analysis)

Next, a description will be given to a method in which the principle component analysis is performed by using the matrix Z formed by the above procedure, and its interpretation is performed in the clinical field (incidentally, see, with respect to the principal component analysis, for example, "Haruo Yanai "Multivariate Data Analysis Method" Asakura Shoten"). Here, only minimum expressions necessary for performing the principal component analysis will be indicated.

First, a covariance matrix S is obtained.

$$S=(1/n)ZZ^T$$

(n: the number of times of measurement in the time direction, in this example, because of 9 times and 6 sets, n=54). Next, an eigenvalue problem set forth below is solved.

$$Sa_j=\lambda_j a_j$$

The covariance matrix S has an eigenvalue $\lambda_j$ of the number of times of blink intervals, and an eigenvector $a_j$. For example, under the measurement condition here, j=1 to 6, and 6 eigenvalues and 6 eigenvectors can be obtained.

A matrix Z' on which the principal component analysis has been performed is obtained as described above ((C') in FIG. 6). The matrix Z' is expressed as a following expression.

$$Z'=(a_1 a_2, \ldots a_m)$$

(m: the number of sets by blinking, and in this example, 6).

Here, a transformation quite opposite to the transformation into the one-dimensional array by the processing from (b) to (c) in FIG. 6 is performed, so that a two-dimensional matrix relevant to the eigenvectors is obtained ((d) in FIG. 6). The two-dimensional matrix of each measurement unit has 25 rows and 9 columns, the 25 rows correspond to the Zernike polynomials in sequence similarly to the case of the input matrix, and 9 columns correspond to measurement times of from 1 second to 9 seconds. However, there is no time relation among 6 vectors of the respective measurement units. These six vectors have contribution ratios to the whole information of the aberration and change, which are in proportion to the magnitudes of the corresponding eigenvalues.

Figure 7:
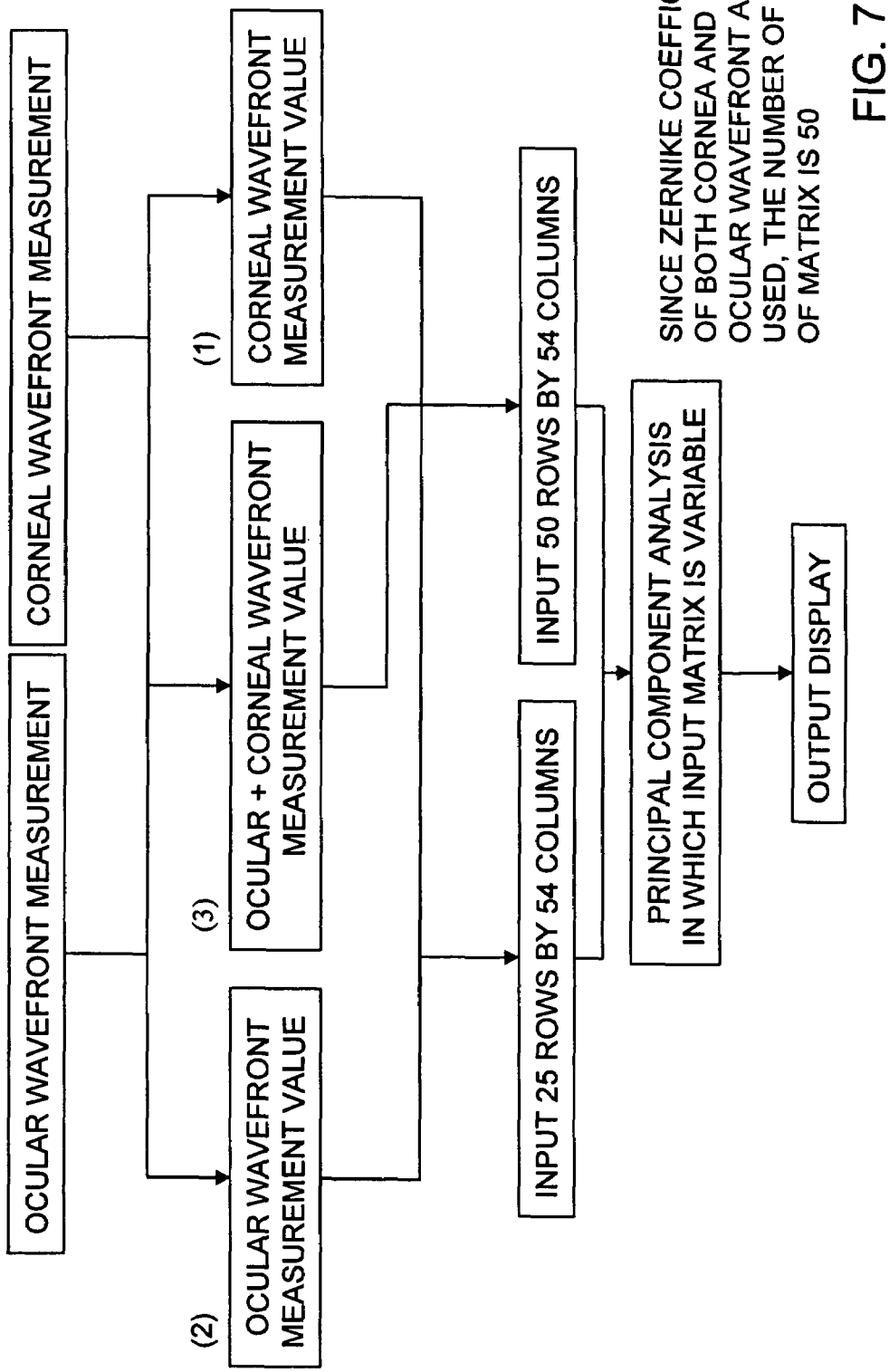
FIG. 7 is an explanatory view of measurement and analysis.

FIG. 7 is an explanatory view of measurement and analysis in each of measurement modes.

(1) Corneal Wavefront Measurement Mode

In this measurement mode, firstly, corneal wavefront measurement is performed, and corneal wavefront measurement values are obtained. The form of the corneal wavefront measurement values in this example has 25 rows and 54 columns. The measurement values of 25 rows by 54 columns are made input data, the principal component analysis is performed, and the result of the analysis is outputted and displayed.

(2) Ocular Wavefront Measurement Mode

In this measurement mode, firstly, ocular wavefront measurement is performed, and ocular wavefront measurement values are obtained. The form of the ocular wavefront measurement values in this example has 25 rows and 54 columns. The measurement values of 25 rows by 54 columns are made input data, the principal component analysis is performed, and the result of the analysis is outputted and displayed.

(3) Both-Wavefront Measurement Mode of the Corneal Wavefront Measurement and the Ocular Wavefront Measurement In this measurement mode, both the corneal wavefront measurement and the ocular wavefront measurement are performed, and the corneal wavefront measurement values and the ocular wavefront measurement values are obtained. In this example, each of the cornea and the wavefront aberration has a form of 25 rows by 54 columns, the measurement values of 25 rows by 54 columns are made input data for each, the principal component analysis is performed, and the result of the analysis is outputted and displayed. Besides, since the Zernike coefficients from both the cornea and the ocular wavefront are used, the number of rows of the matrix is 50, the form has 50 rows and 54 columns, the measurement values of 50 rows by 54 columns are made input data, the principal component analysis is performed, and the result of the analysis can also be outputted and displayed.

Incidentally, the input matrix of the principal component analysis can be made variable.

(Flowchart)

Figure 8:
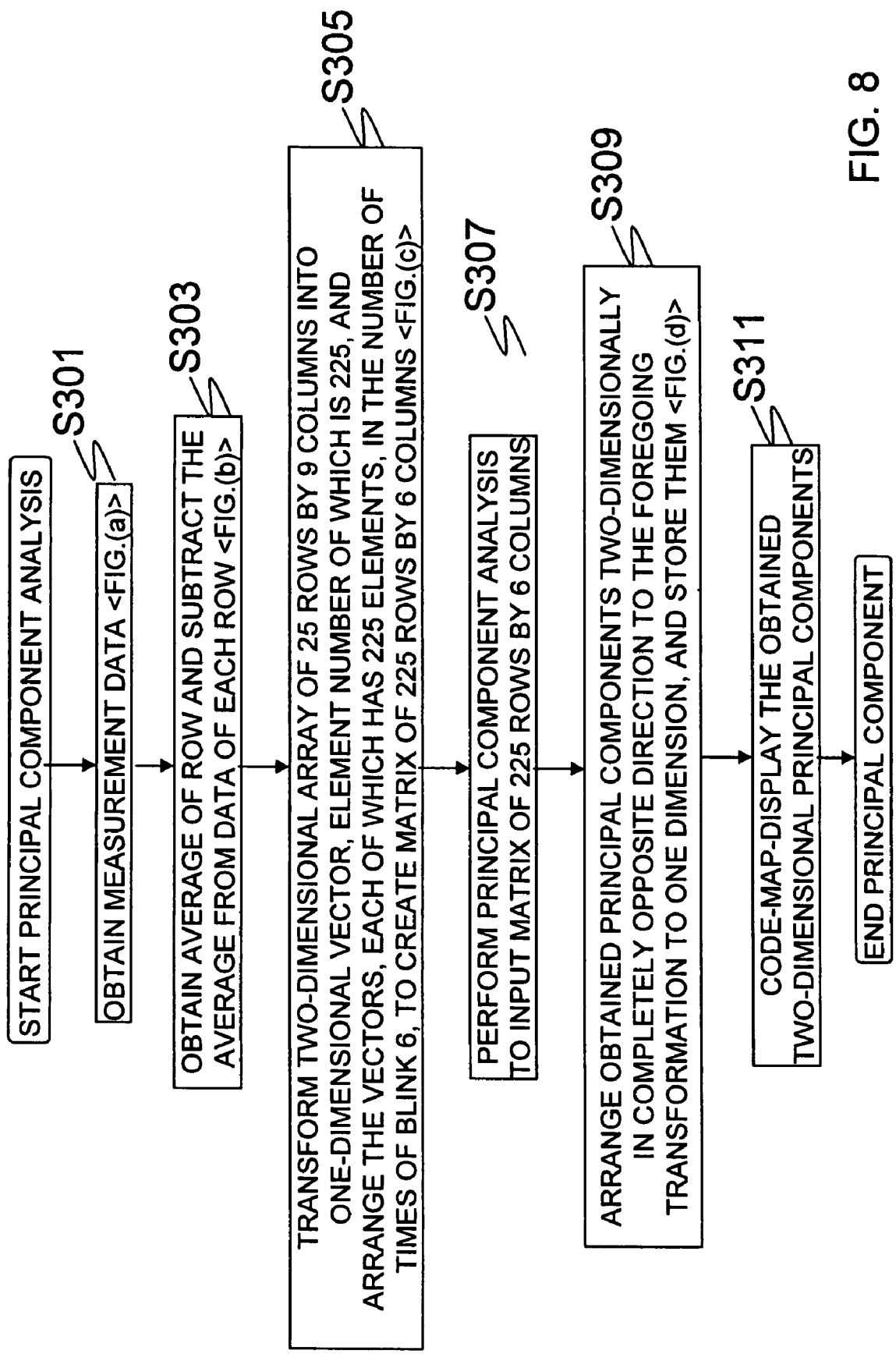
FIG. 8 is a flowchart of the principal component analysis.

FIG. 8 shows a flowchart of the principal component analysis.

First, the analysis part 604 reads measurement data from the memory 800. Alternatively, the analysis part obtains measurement data from the measurement part 601 (step S301). In this example, as described above, the form of the measurement data is a matrix of 25 rows by 54 columns, the vertical 25 rows correspond to the Zernike coefficients, and the horizontal 54 columns correspond to the measurement points in the time direction. Besides, in the measurement data, 54 points in the time direction correspond to measurement data of (6 blink intervals)×(9 points in the time direction). Next, the analysis part 604 takes an average for the row of the measurement data, and subtracts the average from the data of each row (step S303). Next, the analysis part 604 regards the whole data (25 rows by 54 columns) as 6 arrays, each having 25 rows and 9 columns, for the respective blink intervals, transforms the two-dimensional array of 25 rows by 9 columns into a one-dimensional vector (the number of elements is 225), and further, the analysis part 604 arranges the one-dimensional data in the P-th blink interval at the P-th column (step S305). In this example, vectors each of which has 225 elements and the number of which is the number of times of blink, that is, 6 are arranged to create a matrix of 225 rows by 6 columns. Next, the analysis part 604 performs the principal component analysis while the matrix of 225 rows by 6 columns is made input data (step S307). The analysis part 604 transforms the obtained principal components into a two-dimensional array in the completely opposite direction to the transformation into the one-dimensional array at step S305, and stores the two-dimensional principal components into the memory 800 (step S309). The analysis part 604 reads the obtained two-dimensional principal components from the memory 800, executes the processing for display, and displays the gray scale map or color code map on the display part 700 (step S311).

5-4. Code Map

FIG. 9 is a view of results of principal components in a normal example. Besides, FIG. 10 is a view of results of principal components in a slight dry eye.

The code map includes a color code map and a gray scale map. Here, as an example, there are presented the results of a normal eye and a slight dry eye which is a dry eye according to a gray scale map although it is a normal eye.

(a), (b) and (d) of FIG. 9 and FIG. 10 respectively correspond to (a), (b) and (d) in FIG. 6. In the gray scale map, the Zernike coefficients are vertically arranged as c(2,−2), c(2,0), . . . , c(6,6), and the horizontal direction basically indicates a time. After the principal component analysis, 6 principal components are horizontally arranged, and each of them in the horizontal direction (that is, ⅙) corresponds to 10 seconds of the blink interval.

In this example, as a result of the principal component analysis, the uneven coefficients are uniformed into the first principal component, and information compression is successful. On the other hand, in the slight dry eye, it appears that the data compression through the principal component does not succeed very much. The information is not gathered in the left first and second principal components, and fine vibrations remain toward the sixth principal component, and in high-order components of the Zernike coefficients. When it is assumed that a change in aberration due to the tear fluid is not temporally uniform on the pupil (when it is assumed that the changes of the respective coefficients are not correlated to each other), it can be explained that the information compression is not successful in the principal component analysis.

5-5. Dry Eye Index

In the automatic diagnosis at step S113, the analysis part 604 calculates a following dry eye index, and the arithmetic part 600 may display the calculation result on the display part 700.

In the method of the principal component analysis proposed here, since the change in the aberration can be judged by merely seeing one illustrated pattern, it can be said that the method is suitable for use at a clinical site. Here, as a tool to perform the automatic diagnosis of dry eye, the dry eye index is defined as follows.

As the dry eye index, for example, the contribution ratio (%) of the first principal component, or the index based on the sum of dispersion degrees of all principal components is mentioned. The first example is the contribution ratio of the first principal component $\lambda_1$ obtained from the principal component analysis described here.

The calculation method is as follows.

$$\text{Dry eye } index_1 = \frac{\text{Magnitude of first principle component } \lambda_1}{\sum_{i=1}^{6} \text{Magnitude of } i\text{-th principle component } \lambda_i}$$

The second example is the sum of all principal components ($\lambda_1$ to $\lambda_6$) as indicated by a following expression.

$$\text{Dry eye } index_2 = \sum_{i=1}^{6} \text{Magnitude of } i\text{-th principle component } \lambda_i$$

It is estimated that as the dry eye index 1 becomes small, or as the dry eye index 2 becomes large, the degree of dry eye is large.

6. Details of Corneal Wavefront Aberration Measurement

Hereinafter, with respect to the wavefront aberration of a tear film surface shape of a corneal surface, the details of the measurement processing will be described.

6-1. Measurement of Corneal Shape: S107

Figure 11:
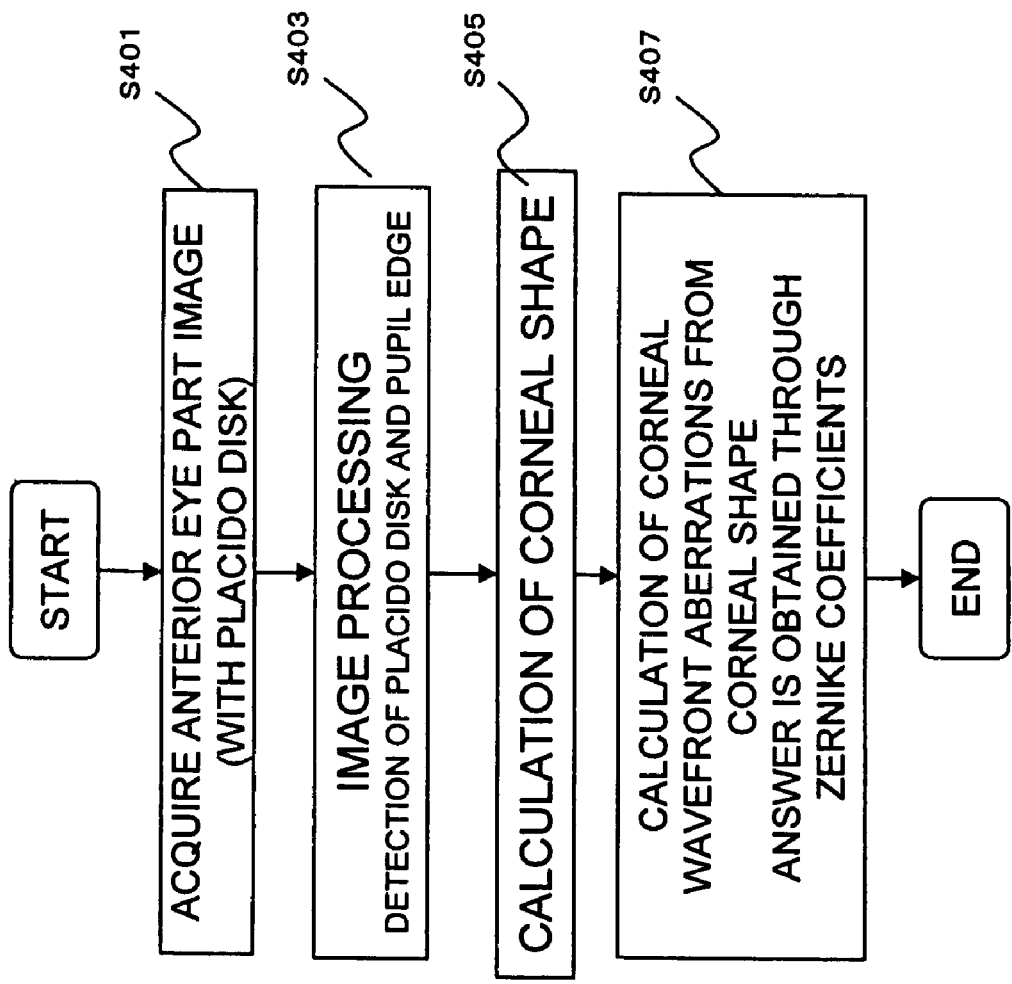
FIG. 11 is a flowchart of corneal shape measurement.

FIG. 11 is a flowchart of a corneal shape measurement. This corresponds to the step S107 of FIG. 3.

First, the measurement part 601 acquires an anterior eye part image (with a Placido disk) (S401). The acquired image is suitably stored in the memory 800 or the like. The measurement part 601 carries out an image processing of the anterior eye part image, and detects the Placido disk and the pupil edge (S403). The measurement part 601 calculates the corneal shape on the basis of the detected data (S405). The measurement part 601 calculates corneal wavefront aberrations from the calculated corneal shape (S407). Here, the calculation result is obtained as Zernike coefficients.

Hereinafter, the details of the respective steps will be described.

(Anterior Eye Part Image: S401)

At step S401, the following anterior eye part image is acquired.

Figure 12A:
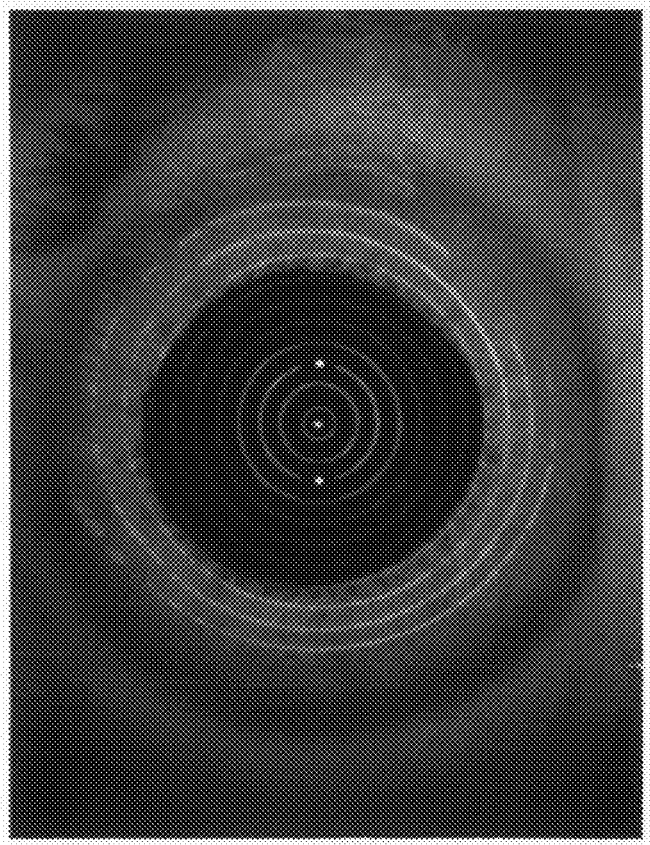
FIGS. 12A and 12B are explanatory views of a time change in corneal shape.
Figure 12B:
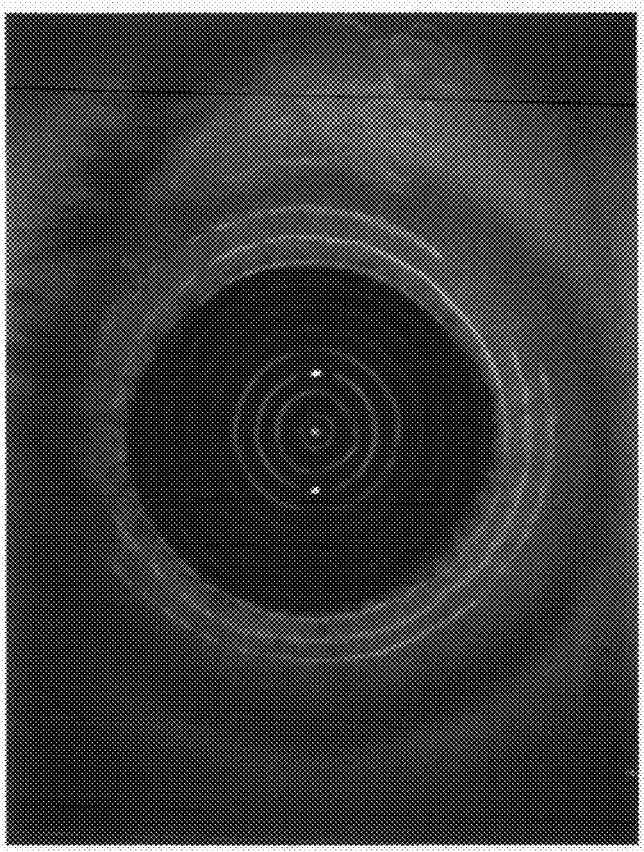

FIGS. 12A and 12B are explanatory views of the temporal change of the corneal shape.

FIG. 12A shows a state immediately after the measurement start, and when analyzed, the corneal wavefront aberrations are relatively small. On the other hand, FIG. 12B shows a state where 30 seconds has passed since the measurement started, and the image of the Placido disk blurs, and when analyzed, the corneal wavefront aberrations are relatively large.

Figure 13B:
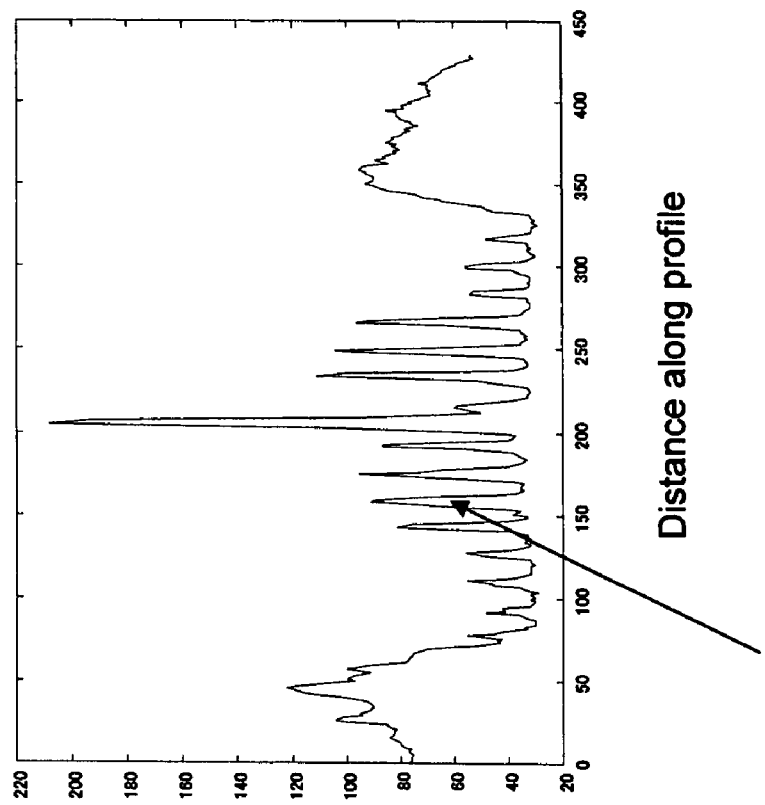
FIGS. 13A and 13B are explanatory views of a time change in blur of a Pracido ring image.
Figure 13A:
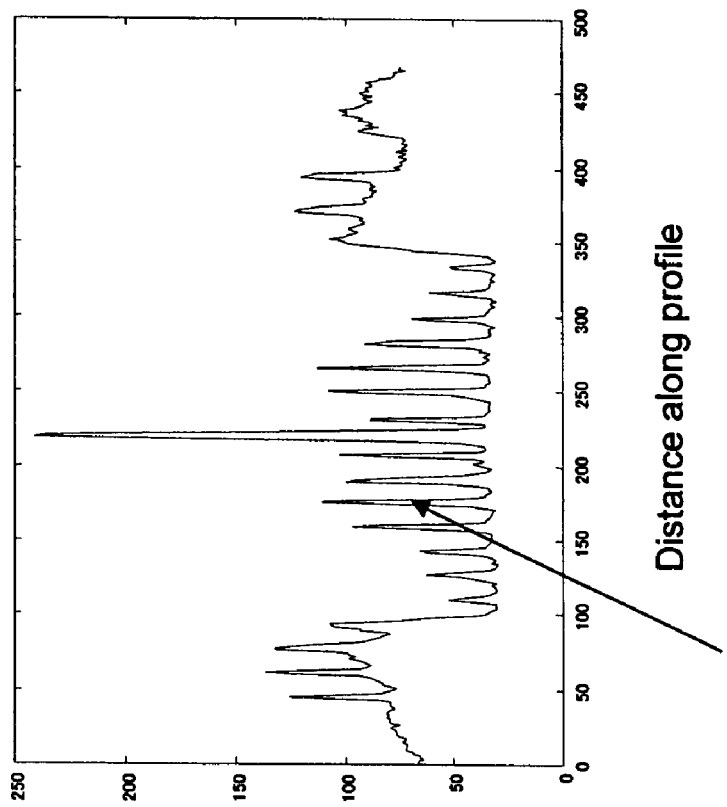

Incidentally, FIGS. 13A and 13B are explanatory views of the temporal change of the blur of the Placido disk image (profile of cross section passing through a center bright point of the Placido disk image).

FIG. 13A shows the state immediately after the measurement start, and as indicated by an arrow, a reflected image is clear, and the width of the reflected image of the Placido disk is narrow. On the other hand, FIG. 13B shows the state where a predetermined time has passed since the measurement started, and as indicated by an arrow, the reflected image blurs, and the width of the reflected image of the Placido disk is wide.

(Image Processing: S403)

Figure 14:
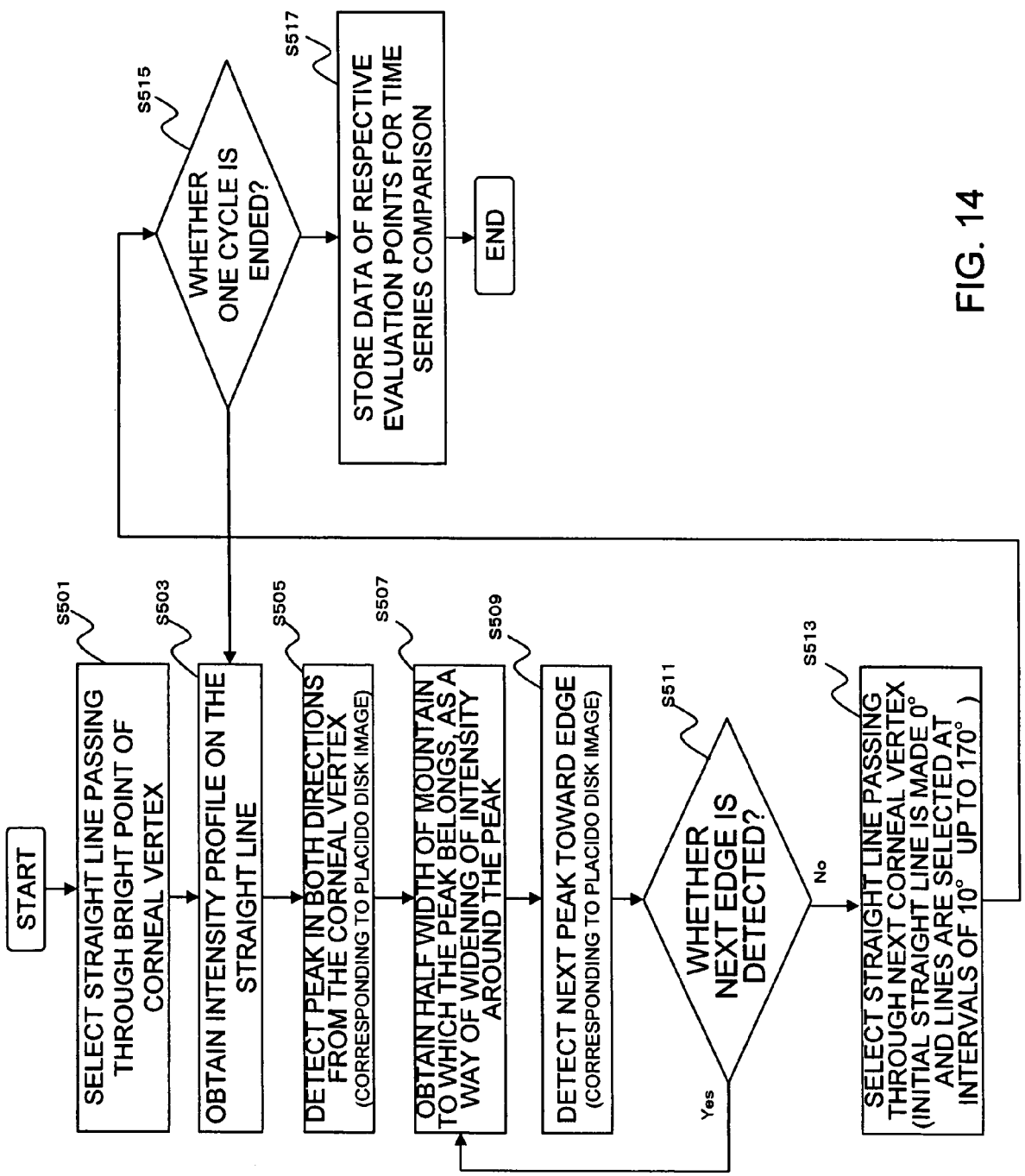
FIG. 14 is a flowchart of image processing of detection of a Pracido ring and a pupil edge.

FIG. 14 shows a flowchart of an image processing of detection of the Placido disk and the pupil edge. This corresponds to the step S403.

Figure 15:
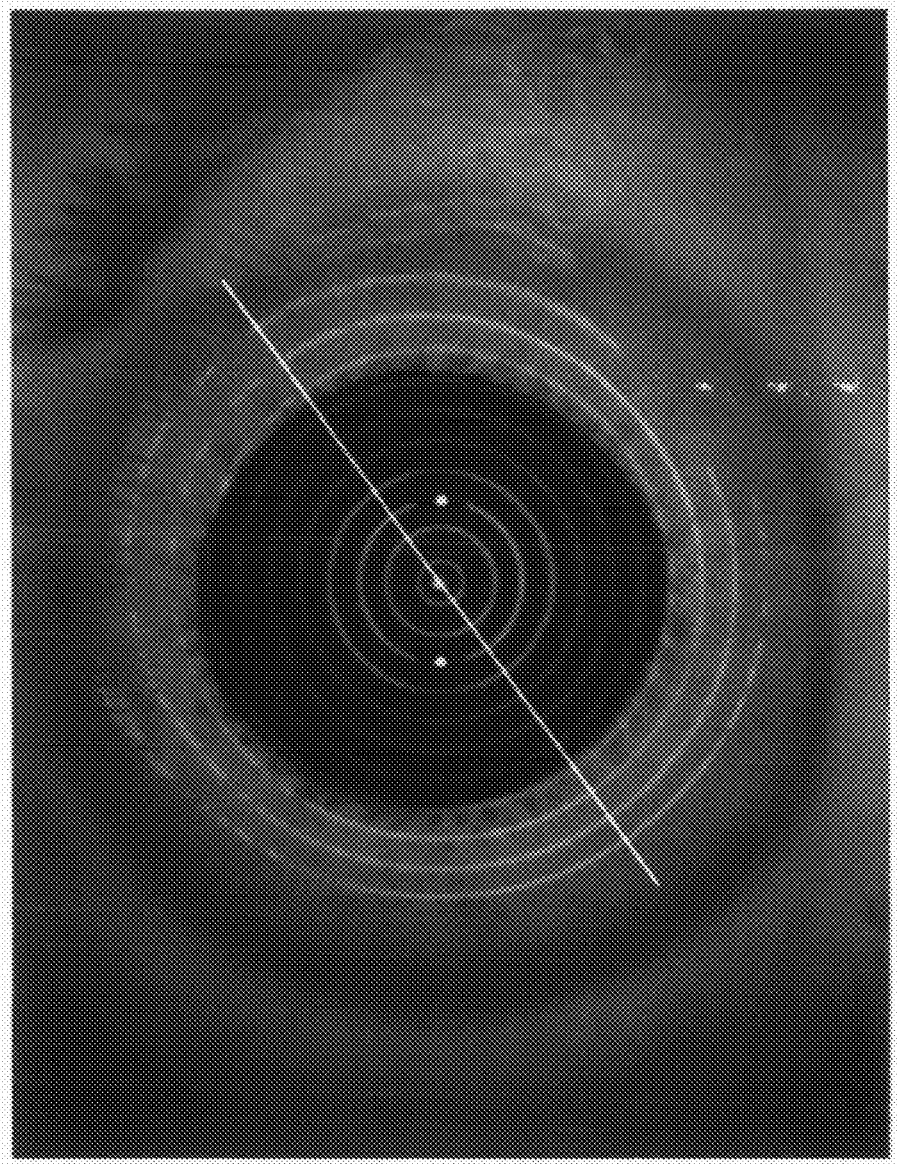
FIG. 15 is an explanatory view of image processing.

Besides, FIG. 15 is an explanatory view of the image processing.

First, as shown in FIG. 15, the measurement part 601 selects a straight line passing through a bright point of the vertex of the cornea on the basis of the acquired anterior eye part image (S501). Next, as shown in FIGS. 13A and 13B, the measurement part 601 obtains an intensity profile on the straight line (S503). On the basis of the profile, the measurement part 601 detects peaks in both directions from the vertex of the cornea (S505) (corresponding to the Placido disk image). Besides, as a way of widening of intensity around the peak, the measurement part 601 obtains the half width of a mountain to which the peak belongs (S507). Further, the measurement part 601 detects a next peak toward the edge (S509) (corresponding to the Placido disk image). The measurement part 601 judges whether the next edge can be detected (S511), and repeats the steps S507 and S509 until it becomes impossible to detect the edge.

Next, the measurement part 601 selects a straight line passing through a next vertex of the cornea (S513) (for example, the first straight line is made 0 degree, and lines are selected at intervals of 10 degrees up to 170 degrees). The measurement part 601 judges whether one cycle is ended (S515), and repeats the processing subsequent to the step S503 until one cycle is ended. Thereafter, the measurement part 601 stores the data of the respective evaluation points into the memory 800 for time series comparison (S517). In the data of the corneal shape obtained in this way, for example, the peak value or the coordinate value (ring position) of the barycenter and the intensity and/or the half width are stored in a time series for every ring and angle.

(Calculation Method of Corneal Shape: S405)

Hereinafter, the step S405 will be described. As an example, a measurement method of the corneal shape will be described along "Rand R H, Howland H C, Applegate R A "Mathematical model of a placido disk karatometer and its implications for recovery of corneal topography", Optometry and Vision Science 74 (1997) p 926-930".

It is assumed that the corneal shape is expressed by a following function.

$$Z_c = f(x, y).$$

Where, x and y indicate coordinates on the cornea.

As shown in FIG. 1, a light beam from a certain Placido disk forms an image at a point on the image pickup device. The position of the Placido disk is made $(x_s, y_s)$, and a point on the cornea conjugate to a corresponding point on the image pickup device of the third light receiving part 41 is made (x, y). A distance from the Placido disk to the reference surface (zero position) of the function of the cornea is made $Z_s$. The relation of these is expressed by a following pair of expressions.

$$x_s = \frac{2(z_s - f)}{f_x^2 + f_y^2 - 1} f_x, \quad y_s = \frac{2(z_s - f)}{f_x^2 + f_y^2 - 1} f_y$$

Where, with respect to $Z_s$, the working distance adjustment part 50 in the drawing can control it or know the accurate distance value. Incidentally, fx denotes a partial differentiation of the function f with respect to x, and $f_y$ denotes a partial differentiation with respect to y.

Here, since the circular Placido disk is adopted, it is rotation symmetric with respect to the axis in the drawing, and is expressed by $$\sqrt{(x_s^2 + y_s^2)} = \text{Constant}$$

and it is assumed that the Constant (constant value) is expressed by $r_s$ (note that this is a value of the apparatus and is already known). Then, since it is known, at the stage of the image processing by the arithmetic part 600, that the position of the point to be measured on the image pickup device belongs to which ring, when the relation of (group of coordinates of points on the image pickup device) versus (radius of ring) is digitized at, for example, 360 points on each ring of eleven rings, the data pairs of the relation corresponding to this can be formed.

Here, the expansion of Zernike polynomials is adopted as the function. Since the normal cornea can be regarded as having no higher order shape change, when an analysis diameter is about 6 mm, the expansion is stopped at approximately the sixth order, and it can be expressed by $$f(x, y) = \sum_{j=-i,-i+2,\ldots,i-2,i}^{6} c_i^j Z_i^j \left( \frac{x}{r_n}, \frac{y}{r_n} \right)$$

Where, $r_n$ indicates a radius to be analyzed, and is used for normalization.

This Zernike expansion is inserted in the two preceding relational expressions, and when it is used that the Placido disk is rotation symmetric, the coefficient $c_i^j$ can be determined by using a nonlinear least square method. When the coefficient determined by this is again inserted in the Zernike expansion, the function f(x, y) is determined, and the corneal shape is obtained.

(Calculation Method of Corneal Wavefront: S407)

Hereinafter, the step S407 will be described. Since the corneal shape is obtained, it is well known that the strict corneal wavefront aberrations in the geometry can be obtained from the ray tracing of an aspheric surface known in optical design. Here, as an example, a method of obtaining a corneal wavefront aberrations very simply will be described.

For example, with respect to the corneal wavefront aberrations with a diameter of 6 mm on the cornea, the corneal shape is approximated by a sphere with appropriate radius (called a reference spherical surface), a difference between the actual corneal shape and the reference spherical surface is obtained, and this is multiplied by the refractive indexes (n−1) of air and the cornea, so that the corneal wavefront aberrations can be obtained from the corneal shape. However, since the spherical aberrations occur from the original reference spherical surface as well, this is added. By this, the corneal wavefront aberrations can be obtained within an approximation accuracy of 5%.

6-2. Ophthalmologic Measurement while a Blink is made a Trigger

Next, a description will be given to an ophthalmologic measurement while a blink is made a trigger.

Steps S101 and S103 areas described above. At step S105, the test subject is instructed to naturally blink in an easy state, and the measurement start button of the input part 650 is pressed. Next, at step S107 and S109, the arithmetic part 600 starts a Hartmann continuous measurement (intervals of one second) by the measurement part 601. Further, here, the measurement part 601 starts an anterior eye part continuous measurement (intervals of one second), obtains the histogram relating to the brightness every time, and judges the blink from this.

Figure 16:
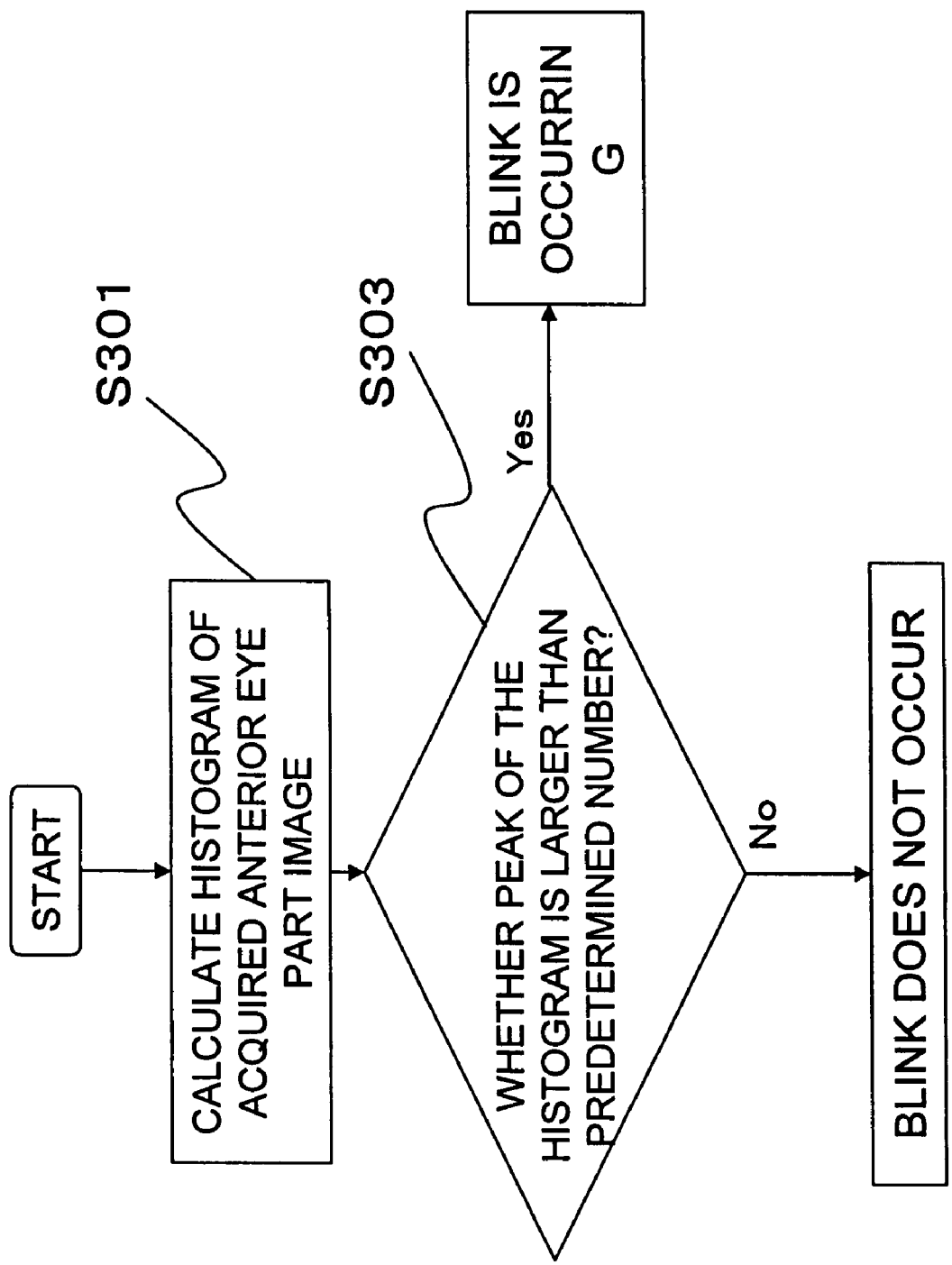
FIG. 16 is a judgment flowchart of blinking.
Figure 18A:
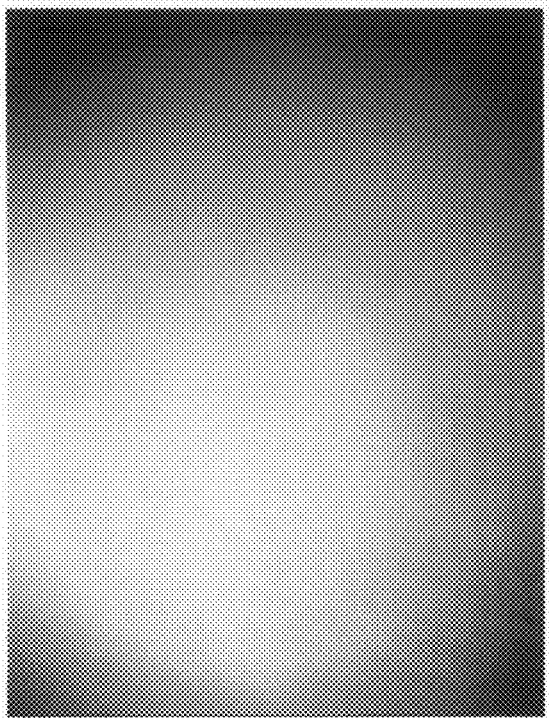
FIGS. 18A and 18B are explanatory views concerning a histogram when a blink is occurring.
Figure 18B:
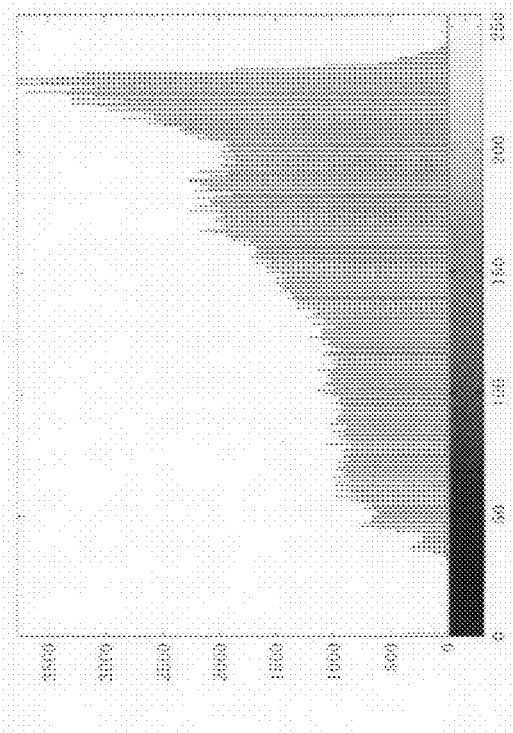

FIG. 16 is a judgment flowchart of the blink. Besides, FIGS. 17A and 17B and FIGS. 18A and 18B are respectively explanatory views of histograms at the time when a blink does not occur and at the time when a blink is occurring. FIGS. 17A and 18A show anterior eye part images, and FIGS. 17B and 18B show histograms.

When the judgment flowchart of the blink is started, the judgment part 602 of the arithmetic part 600 calculates the histogram of the acquired anterior eye part image (S301). The judgment part 602 compares the peak of the histogram with a predetermined number (for example, 150). Here, in the case where the peak is larger than the predetermined number, it is judged that the blink is occurring (see FIGS. 18A and 18B), and on the other hand, in the case where the peak is smaller, it can be judged that the blink does not occur (see FIG. 17).

Next, returning to the main flow, for example, the test subject is instructed to blink at a predetermined timing after one blink occurs. When the end time of the final blink is made to, the judgment part 602 ends the measurements of the Hartmann and the anterior eye part when a predetermined time has passed since $t_0$. In this case, by keeping on obtaining anterior eye images in real time, and the interval of blink can also be measured with accuracy by the foregoing judgment. Incidentally, as the alignment during the measurement, since the measurement is carried out for, for example, about 70 seconds, it may be preferable to use an auto alignment which makes continuous measuring possible by shifting the axis of lens to follow the motion of the subject eye. Besides, a mechanism can also be provided in which an operator makes an alignment manually.

7. Example of Binocular Simultaneous Measurement

Figure 19:
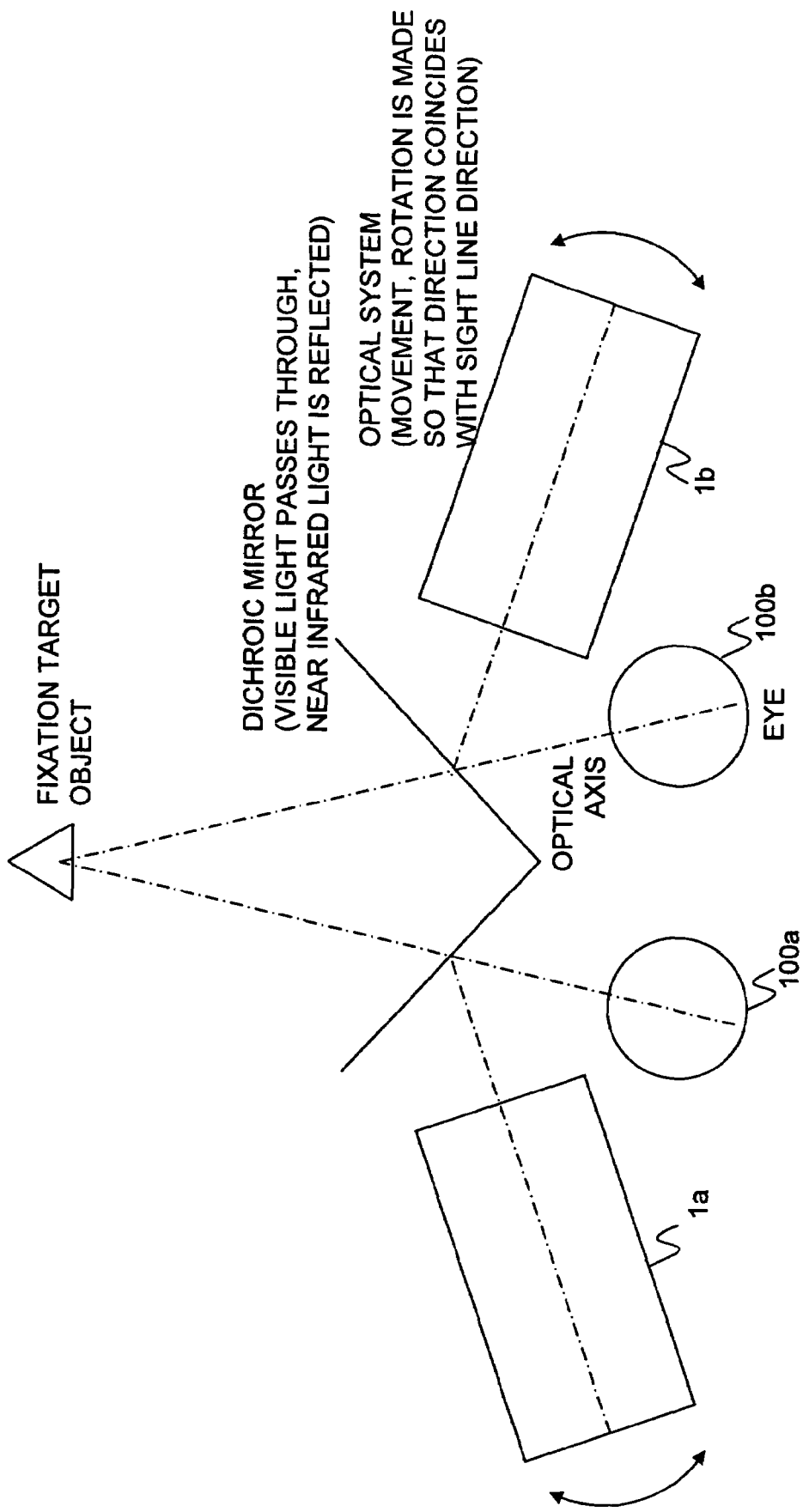
FIG. 19 is a structure view of an ophthalmologic system (1) for both-eye simultaneous measurement.

FIG. 19 and FIG. 20 show an ophthalmologic systems (1) and (2) structural view for a binocular simultaneous measurement.

These ophthalmologic systems (1) and (2) both include optical systems 1a and 1b of FIG. 1 for both eyes 100a and 100b, and those can be independently adjusted and an alignment becomes possible for both the eyes. Then, although the description up to the above relates to a measurement for only one eye, a measurement can be made simultaneously for both the eyes by using the two apparatuses. Even in the case of a single eye measurement, both eyes must be opened, and a measurement of another single eye has not been capable of being performed for a while after the single eye measurement. However, in this case, there is a merit that the measurement can be certainly performed for both the eyes.

8. Zernike Analysis and RMS

Next, a Zernike analysis will be described. A method of calculating Zernike coefficients $c_i^{2j-1}$ from generally known Zernike polynomials will be described. The Zernike coefficients $c_i^{2j-1}$ are important parameters for grasping the optical characteristics of the subject eye 100 on the basis of, for example, the inclination angle of the light flux obtained by the first light receiving part 21 through the Hartmann plate 22.

A wavefront aberration $W(X, Y)$ of the subject eye 100 is expressed by a following expression using the Zernike coefficients $c_i^{2j-1}$ and Zernike polynomials $Z_i^{2j-1}$.

$$W(X, Y) = \sum_{i=0}^{n} \sum_{j=0}^{i} c_i^{2j-i} Z_i^{2j-i}(X, Y)$$

Where, $(X, Y)$ are vertical and horizontal coordinates of the Hartmann plate 22.

Besides, with respect to the wavefront aberration $W(X, Y)$, when the vertical and horizontal coordinates of the first light receiving part 21 are made $(x, y)$, the distance between the Hartmann plate 22 and the first light receiving part 21 is made f, and the movement distance of a point image received by the first light receiving part 21 is made $(\Delta x, \Delta y)$, the relation indicated by a following expression is established.

$$\frac{\partial W(X, Y)}{\partial X} = \frac{\Delta x}{f},$$

$$\frac{\partial W(X, Y)}{\partial Y} = \frac{\Delta y}{f}$$

Where, the Zernike polynomials $Z_i^{2j-1}$ is expressed by a following expression.

$$Z_n^m = R_n^m(r) \left\{ \frac{\sin}{\cos} \right\} \{m\theta\}$$

$m > 0$ sin $m \leq 0$ cos $$R_n^m(r) = \sum_{S=0}^{(n-m)/2} (-1)^S \frac{(n-S)!}{S! \left\{ \frac{1}{2}(n-m) - S \right\}! \left\{ \frac{1}{2}(n+m) - S \right\}!} r^m$$

Incidentally, with respect to the Zernike coefficients $c_i^{2j-1}$, specific values can be obtained by minimizing the square error expressed by a following mathematical expression.

$$S(x) = \sum_{i=1}^{data\ number} \left[ \left\{ \frac{\partial W(X_i, Y_i)}{\partial X} - \frac{\Delta x_i}{f} \right\}^2 + \left\{ \frac{\partial W(X_i, Y_i)}{\partial Y} - \frac{\Delta Y_i}{f} \right\}^2 \right]$$

Where, $W(X, Y)$: wavefront aberration, $(X, Y)$: Hartmann plate coordinates, $(\Delta x, \Delta y)$: movement distance of the point image received by the first light receiving part 21, and f: distance between the Hartmann plate 22 and the first light receiving part 21.

The arithmetic part 600 calculates the Zernike coefficients $c_i^{2j-1}$, and obtains the optical characteristics, such as spherical aberrations, coma aberrations, and astigmatism by using these. Besides, the arithmetic part 600 calculates RMS of the aberration $RMS_i^{2-1}$ by using the Zernike coefficients $c_i^{2j-i}$.

$$RMS_i^{2j-i} = \sqrt{\frac{\varepsilon_i^{2j-i}}{2(i+1)}} c_i^{2j-i}$$

$$\left( \varepsilon_i^{2j-i} = 2(2j = i), \varepsilon_i^{2j-i} = 1(2j \neq i) \right)$$

The invention can be widely applied to an ophthalmologic measuring apparatus, a surgical apparatus and the like.

What is claimed is:

1. An ophthalmologic measuring apparatus comprising:
   an illuminating optical system including an illuminating light source to illuminate a subject eye;
   a light receiving optical system including a light receiving part to receive a reflected light flux from the subject eye illuminated with an illumination light flux of the illuminating optical system and to form a received light signal;
   a measurement part that, based on the received light signal formed by the light receiving part, measures a wavefront aberration at a predetermined measurement interval to obtain one-dimensional wavefront aberration data by Zernike coefficients, and obtains wavefront aberration data of a two-dimensional matrix form to represent a time course by grouping Zernike coefficients of each wavefront aberration of the subject eye in a blink interval from a blink to a next blink with respect to a first to an n-th (n is an integer of 2 or more) blink intervals;
   an analysis part that transforms the two-dimensional matrix to a new one-dimensional column vector with respect to the first to the n-th blink intervals measured by the measurement part, arranges a one-dimensional array of the wavefront aberration in a p-th ($1 \leq p \leq n$) blink interval at a p-th column to create a two-dimensional matrix, and performs a principal component analysis processing on the two-dimensional matrix; and
   a display part to display a processing result of the analysis part.

2. The ophthalmologic measuring apparatus according to claim 1, wherein the analysis part obtains an average value of the coefficients in the time direction with respect to wavefront aberration data of a two-dimensional matrix form to represent a time course by grouping Zernike coefficients of each wavefront aberration of the subject eye in a blink interval from a blink to a next blink, and subtracts the average value of each element from each element of the wavefront aberration data of a two-dimensional matrix form.

3. The ophthalmologic measuring apparatus according to claim 1, wherein the analysis part, with respect to principal components obtained by the principal component analysis processing, for each of the principal components of the two-dimensional matrix, converts the one-dimensional array at the p-th column into two-dimensional data to represent the time course of each wavefront aberration, and arranges the first to the n-th wavefront aberration data, reversely to a manner in which each of the wavefront aberration data concerning the first to the n-th blink intervals measured by the measurement part is arranged one-dimensionally, to obtain a two-dimensional space representing a time change of each wavefront aberration, and the display part displays a code map based on the obtained two-dimensional space.

4. The ophthalmologic measuring apparatus according to claim 1, wherein the display part displays, as a code map, typical gray codes or color codes of a normal, a light dry eye, an intermediate dry eye, and a serious dry eye, for judgment of a measured case, on a screen, or, the display part displays these gray scale codes or color codes on the screen by a simple operation.

5. The ophthalmologic measuring apparatus according to claim 1, further comprising a sign signal formation part to encourage a subject to blink, wherein the measurement part measures the wavefront aberration of the subject eye varying with elapsed time from an end of the blink of the subject.

6. The ophthalmologic measuring apparatus according to claim 1, further comprising a judgment part to detect a blink of a subject, wherein when the judgment part detects the blink of the subject, the measurement part measures the wavefront aberration of the subject eye varying with elapsed time from an end of the blink of the subject.

7. The ophthalmologic measuring apparatus according to claim 1, wherein the illuminating optical system illuminates the subject eye with the illumination light flux forming substantially a point light source on an ocular fundus of the subject eye, or with the illumination light flux converging on the center of curvature of a cornea, the light receiving optical system includes plural light receiving parts that receive the reflected light flux from the ocular fundus of the subject eye illuminated with the illumination flux of the illuminating optical system and from a corneal surface, and form a first and a second received light signals, and the measurement part measures a wavefront aberration of the whole subject eye based on the reflected light flux from the ocular fundus, and measures a corneal aberration of the cornea of the subject eye based on the reflected light flux from the corneal surface.

8. The ophthalmologic measuring apparatus according to claim 7, wherein the measurement part simultaneously measures the wavefront aberration of the whole subject eye based on the reflected light flux from the ocular fundus, and the cornea aberration of the cornea of the subject eye based on the reflected light flux from the corneal surface.

9. The ophthalmologic measuring apparatus according to claim 1, wherein the illuminating optical system illuminates the subject eye with the illumination light flux forming substantially a point light source at an ocular fundus of the subject eye, the light receiving optical system receives the reflected light flux from the ocular fundus of the subject eye illuminated with the illumination light flux of the illuminating optical system and forms the received light signal, and the measurement part measures a wavefront aberration of the whole subject eye based on the reflected light flux from the ocular fundus.

10. The ophthalmologic measuring apparatus according to claim 1, wherein the illuminating optical system illuminates the subject eye with the illumination light flux converging on the center of curvature of a cornea of the subject eye, the light receiving optical system receives the reflected light flux from a corneal surface illuminated with the illumination light flux of the illuminating optical system and forms the received light signal, and the measurement part measures a corneal aberration of the cornea of the subject eye based on the reflected light flux from the corneal surface.

11. The ophthalmologic measuring apparatus according to claim 1, wherein the illuminating optical system illuminates the subject eye with the illumination light flux to form substantially a point light source on both ocular fundi of a subject and/or with the illumination light flux converging on the centers of curvature of corneas of both eyes of the subject, the light receiving optical system receives the reflected light flux from the ocular fundi of both the eyes of the subject illuminated with the illumination light flux of the illuminating optical system and/or the reflected light flux from corneal surfaces of both the eyes of the subject, and forms a first received light signal and/or a second received light signal, and the measurement part measures a wavefront aberration of the whole subject eye based on the reflected light flux from the ocular fundus, and/or measures a corneal aberration of the cornea of the subject eye based on the reflected light flux from the corneal surface.

* * * * *